(12) United States Patent
Morse et al.

(10) Patent No.: US 11,406,723 B2
(45) Date of Patent: Aug. 9, 2022

(54) RADIOTHERAPEUTIC AND COMPANION IMAGING AGENTS TO TARGET MC1R

(71) Applicants: H. LEE MOFFITT CANCER CENTER AND RESEARCH INSTITUTE, INC., Tampa, FL (US); UNIVERSITY OF SOUTH FLORIDA, Tampa, FL (US); WAKE FOREST UNIVERSITY, Winston-Salem, NC (US); Modulation Therapeutics, Inc., Morgantown, WV (US)

(72) Inventors: David Morse, Tampa, FL (US); Robert Gillies, Tampa, FL (US); Mark Mclaughlin, Tampa, FL (US); Thaddeus Wadas, Winston-Salem, NC (US); Hyun Joo Kil, Lutz, FL (US); Narges Tafreshi, Tampa, FL (US)

(*) Notice: Subject to any disclaimer, the term of this patent is extended or adjusted under 35 U.S.C. 154(b) by 0 days.

(21) Appl. No.: 16/575,247

(22) Filed: Sep. 18, 2019

(65) Prior Publication Data
US 2020/0108159 A1    Apr. 9, 2020

Related U.S. Application Data

(63) Continuation of application No. 15/172,136, filed as application No. PCT/US2016/031290 on May 6, 2016, now abandoned.

(60) Provisional application No. 62/157,784, filed on May 6, 2015.

(51) Int. Cl.
| | | |
|---|---|---|
| A61K 51/08 | (2006.01) | |
| A61P 35/04 | (2006.01) | |
| A61K 38/00 | (2006.01) | |
| C07K 7/06 | (2006.01) | |
| G01N 33/574 | (2006.01) | |
| C07K 14/705 | (2006.01) | |
| A61K 38/08 | (2019.01) | |

(52) U.S. Cl.
CPC ............ A61K 51/088 (2013.01); A61K 38/08 (2013.01); A61P 35/04 (2018.01); C07K 7/06 (2013.01); C07K 14/705 (2013.01); G01N 33/5743 (2013.01); A61K 38/00 (2013.01)

(58) Field of Classification Search
CPC .................................. A61K 49/00; C07D 7/08
See application file for complete search history.

(56) References Cited

U.S. PATENT DOCUMENTS

| | | | |
|---|---|---|---|
| 4,559,157 A | 12/1985 | Smith et al. | |
| 4,608,392 A | 8/1986 | Jacquet et al. | |
| 4,820,508 A | 4/1989 | Wortzman | |
| 4,938,949 A | 7/1990 | Borch et al. | |
| 4,992,478 A | 2/1991 | Geria | |
| 5,167,649 A | 12/1992 | Zook | |
| 6,960,648 B2 | 11/2005 | Bonny | |
| 6,991,775 B2 * | 1/2006 | Koerner | A61K 49/085 424/1.65 |
| 8,124,054 B2 * | 2/2012 | Hong | C07K 14/685 424/1.69 |
| 8,853,149 B2 | 10/2014 | Hazlehurst et al. | |
| 8,986,651 B2 | 3/2015 | Miao et al. | |
| 9,441,013 B2 | 9/2016 | Gillies et al. | |
| 2002/0035243 A1 | 3/2002 | Imfeld et al. | |
| 2002/0120100 A1 | 8/2002 | Bonny | |
| 2003/0032594 A1 | 2/2003 | Bonny | |
| 2014/0112873 A1 | 4/2014 | Gillies et al. | |
| 2014/0147385 A1 * | 5/2014 | Miao | C07K 14/685 424/1.69 |
| 2014/0322227 A1 | 10/2014 | Hazlehurst et al. | |
| 2015/0104381 A1 | 4/2015 | Maina-Nock et al. | |

FOREIGN PATENT DOCUMENTS

| | | | | |
|---|---|---|---|---|
| WO | 2012/158960 A2 | | 11/2012 | |
| WO | WO 2012/158960 | * | 11/2012 | |
| WO | WO-2012158960 | * | 11/2012 | |
| WO | WO-2012158960 A2 | * | 11/2012 | ............ A61K 47/64 |
| WO | 2013/170066 | | 11/2013 | |
| WO | 2015/048477 | | 4/2015 | |
| WO | 2015/200828 | | 12/2015 | |

OTHER PUBLICATIONS

Zhen Cheng et al. 64Cu-Labeled Alpha-Melanocyte-Stimulating Hormone Analog for MicroPET imaging of Melanocortin 1 Receptor Expression, Bioconjugate Chem, 18, 765-772. (Year: 2007).*
Gebhard et al., "MTI-101 (Cyclized HYD1) Binds a CD44 Containing Complex and Induces Necrotic Cell Death in Multiple Myeloma," Mol. Cancer Ther. 12(11):2446-2458, 2013, (20 pages).
Barkey et al., "Development of melanoma-targeted polymer micelles by conjugation of a Melanocortin 1 Receptor (MC1R) specific ligand," J Med Chem.54(23):8078-8084, 2011.
Bishop et al., "Epidemiology and survival outcomes of ocular and mucosal melanomas: A population-based analysis," Int. J. Canceer 134(12):2961-2971, 2014,.
Cheng et al., "$^{64}$Cu-Labeled Alpha-Melanocyte-Stimulating Hormone Analog for MicroPET Imaging of Melanocortin 1 Receptor Expression," Bioconjugate Chem. 18:765-772, 2007.
López et al., "Melanocortin 1 Receptor is Expressed by Uveal Malignant Melanoma and Can be Considered a New Target for Diagnosis and Immunotherapy," Investigative Ophthalmology & Visual Science 48(3): 1219-1227, 2007.

(Continued)

Primary Examiner — Michael G. Hartley
Assistant Examiner — Jagadishwar R Samala
(74) Attorney, Agent, or Firm — Seed IP Law Group LLP

(57) ABSTRACT

The subject matter disclosed herein relates generally to cancer therapy and to anti-cancer compounds and imaging agents. More specifically, the subject matter disclosed herein relates to agents that target MC1R and their use in the treatment of cancer. Methods of screening for MC1R targeted agents are also disclosed.

12 Claims, 19 Drawing Sheets

Specification includes a Sequence Listing.

(56) References Cited

OTHER PUBLICATIONS

Martinez et al., "Demonstration of a Sucrose-derived Contrast Agent for Magnetic Resonance Imaging of the GI Tract," *Bioorg. Med. Chem. Lett.* 23(7):2061-2064, 2013, (10 pages).

Pereira et al., "Current and emerging treatment options for uveal melanoma," *Clinical Ophthalmology* 7:1669-1682, 2013.

Tafreshi et al., "Synthesis and Characterization of a Melanoma-Targeted Fluorescence Imaging Probe by Conjugation of a Melanocortin 1 Receptor (MC1R) Specific Ligand," *Bioconjug. Chem.* 23(12):2451-2459, 2012.

Tafreshi et al., "In vivo and in silico pharmacokinetics and biodistribution of a melanocortin receptor 1 targeted agent in preclinical models of melanoma," *Mol. Pharm.* 70(8):3175-3185, 2013.

Toyoizumi et al., "Combined Therapy with Chemotherapeutic Agents and Herpes Simplex Virus Type 1 ICP34.5 Mutant (HSV-1716) in Human Non-Small Cell Lung Cancer," *Human Gene Therapy* 10:3913-3929, 1999.

Yang, "Structure, function and regulation of the melanocortin receptors," *Eur. J. Pharmacol.* 660(1):125-130, 2011.

\* cited by examiner

NH —TengalRAM 1) a) Remove Fmoc, b) Couple 4eq. Fmoc-Lys(Alloc)OH, 4eq. HCTU, 8eq. DIEA
2) a) Remove Fmoc, b) Couple 4eq, Fmoc-D-Gly-OH, 4eq. HCTU, 8eq. DIEA
3) a) Remove Fmoc, b) Couple 4eq. Fmoc-Trp(Boc)-OH, 4eq. HCTU, 8eq. DIEA
4) a) Remove Fmoc, b) Couple 4eq, Fmoc-Arg(Pbf)-OH, 4eq. HCTU, 8eq. DIEA
5) a) Remove Fmoc, b) Couple 4eq. Fmoc-D-Phe-OH, 4eq. HCTU, 8eq. DIEA
6) a) Remove Fmoc, b) Couple 4eq, Fmoc-Hs(Trt)-OH, 4eq. HCTU, 8eq. DIEA
7) a) Remove Fmoc, b) Couple 4eq. 4-phenylbutyric acid, 4eq. HCTU, 8eq. DIEA
8) a) Remove Fmoc, b) Couple 4eq, Fmoc-D-Gu(t-butyl)-OH, 4eq. HCTU, 8eq. DIEA
9) a) Remove Fmoc, b) Couple 4eq. Fmoc-D-Gu(t-butyl)-OH, 4eq. HCTU, 8eq. DIEA
10) a) Remove Fmoc, b) Couple 4eq. DOTA-trl-t-butyl-ester, 4eq. HCTU. 8eq DIEA

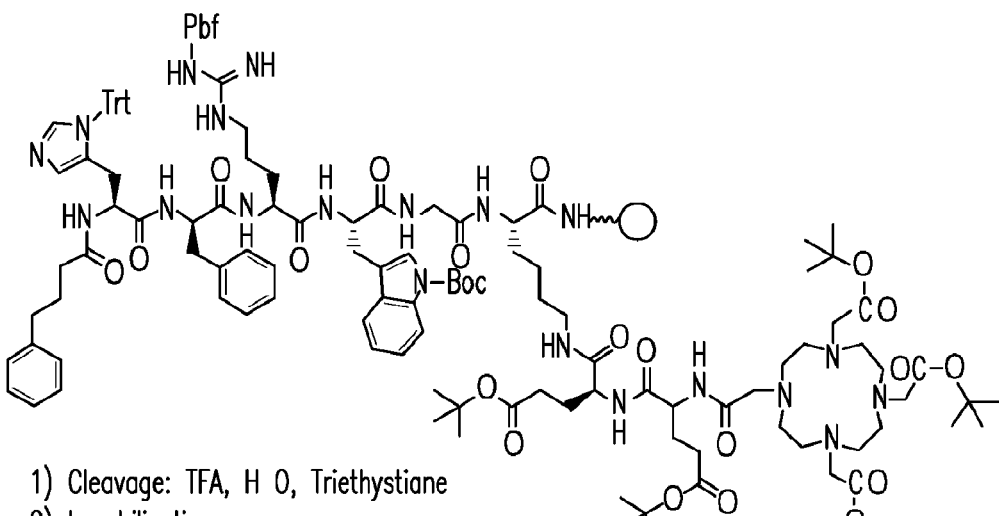

1) Cleavage: TFA, H 0, Triethystiane
2) Lyophilization
3) HPLC Purification

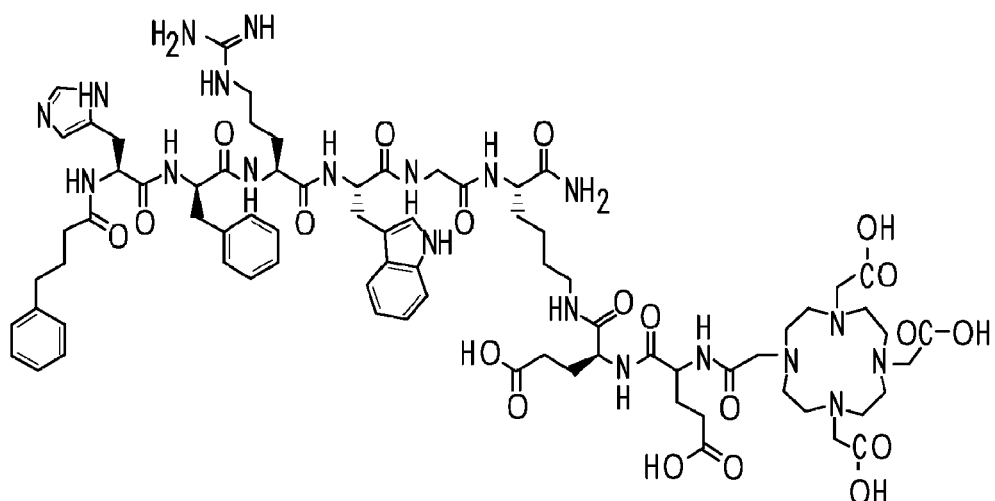

FIG.5

NH₂-Tentagel RAM 1) a) Remove Fmoc, b) Couple 4eq. Fmoc-Lys(alloc)OH, 4eq. HCTU, 8eq. DIEA
2) a) Remove Fmoc, b) Couple 4eq. Fmoc-D-Gly-OH, 4eq. HCTU, 8eq. DIEA
3) a) Remove Fmoc, b) Couple 4eq. Fmoc-Trp(Boc)-OH, 4eq. HCTU, 8eq. DIEA
4) a) Remove Fmoc, b) Couple 4eq. Fmoc-Arg(Pbf)-OH, 4eq. HCTU, 8eq. DIEA
5) a) Remove Fmoc, b) Couple 4eq. Fmoc-D-Phe-OH, 4eq. HCTU, 8eq. DIEA
6) a) Remove Fmoc, b) Couple 4eq. Fmoc-His(Trt)-OH, 4eq. HCTU, 8eq. DIEA
7) a) Remove Fmoc, b) Couple 4eq. 4-phenylbutyric acid, 4eq. HCTU, 8eq. DIEA
8) a) Remove alloc, b) Couple 4eq. Fmoc-D-Lys(Boc)-OH, 4eq. HCTU, 8eq. DIEA
9) a) Remove alloc, b) Couple 4eq. Fmoc-D-Lys(Boc)-OH, 4eq. HCTU, 8eq. DIEA
10) a) Remove Fmoc, b) Couple 4eq. DOTA-trt-t-butyl-ester, 4eq. HCTU, 8eq. DIEA

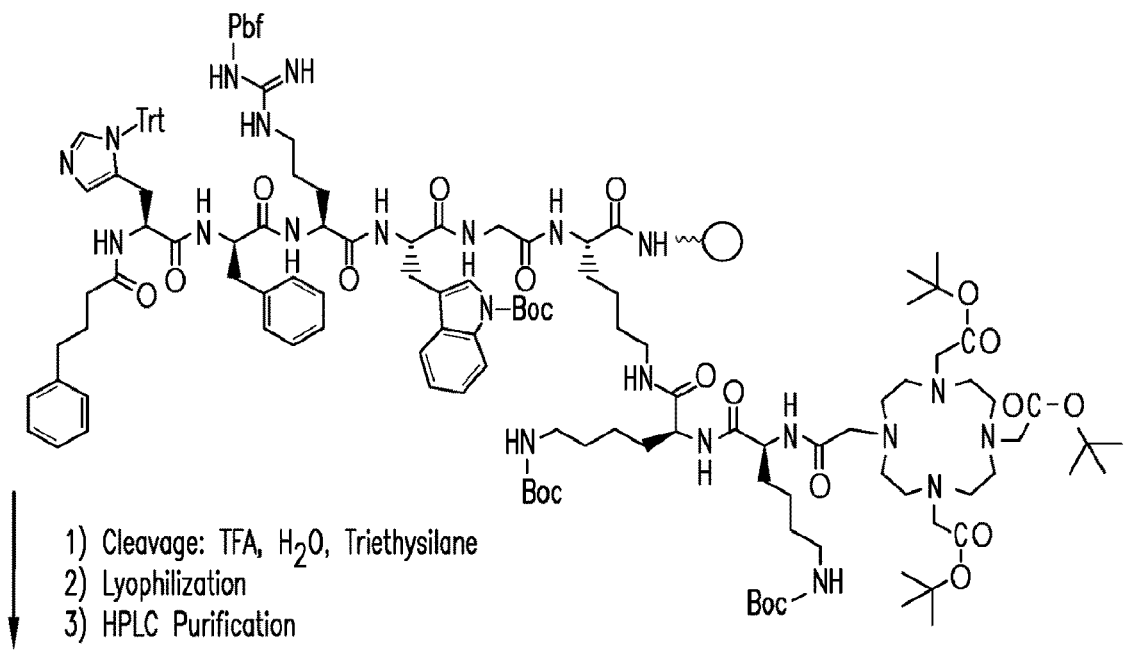

1) Cleavage: TFA, H₂O, Triethysilane
2) Lyophilization
3) HPLC Purification

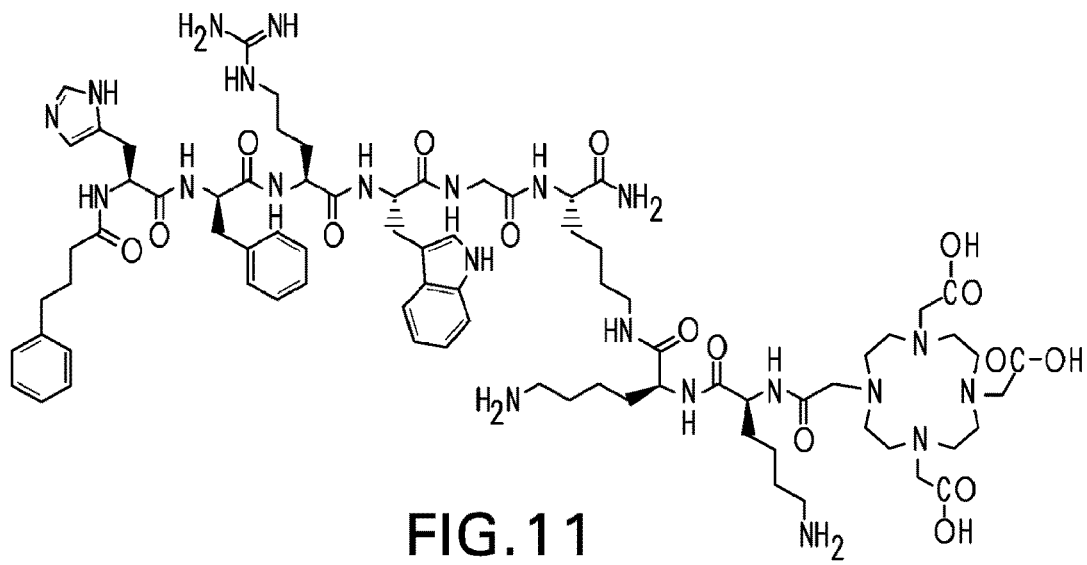

FIG.11

NH₂-Tentagel RAM 1) a) Remove Fmoc, b) Couple 4eq. Fmoc-Lys(alloc)OH, 4eq. HCTU, 8eq. DIEA
2) a) Remove Fmoc, b) Couple 4eq. Fmoc-D-Phe-OH, 4eq. HCTU, 8eq. DIEA
3) a) Remove Fmoc, b) Couple 4eq. Fmoc-Arg(Pbf)-OH, 4eq. HCTU, 8eq. DIEA
4) a) Remove Fmoc, b) Couple 4eq. Fmoc-His(Trt)-OH, 4eq. HCTU, 8eq. DIEA
5) a) Remove Fmoc, b) Couple 4eq. Fmoc-Gly-OH, 4eq. HCTU, 8eq. DIEA
6) a) Remove Fmoc, b) Couple 4eq. Fmoc-Trp(Boc)-OH, 4eq. HCTU, 8eq. DIEA
7) a) Remove Fmoc, b) Couple 4eq. 4-phenylbutyric acid, 4eq. HCTU, 8eq. DIEA
8) a) Remove ALLOC, b) Couple 4eq. Fmoc-hexanoic acid, 4eq. HCTU, 8eq. DIEA
9) a) Remove Fmoc, b) Couple 4eq. DOTA-Trt-t-Butyl-ester, 4eq. HCTU, 8eq. DIEA

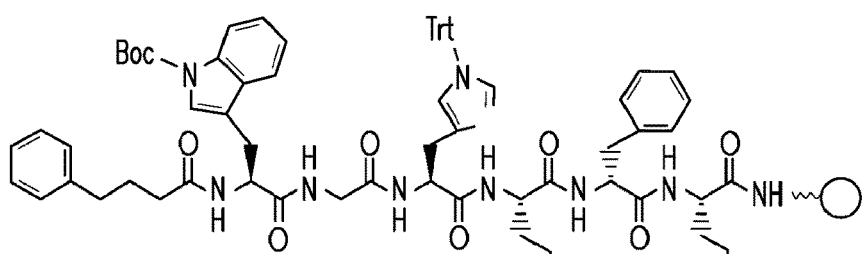

1) Cleavage: TFA, H₂O, Triethysilane
2) Lyophilization
3) HPLC Purification

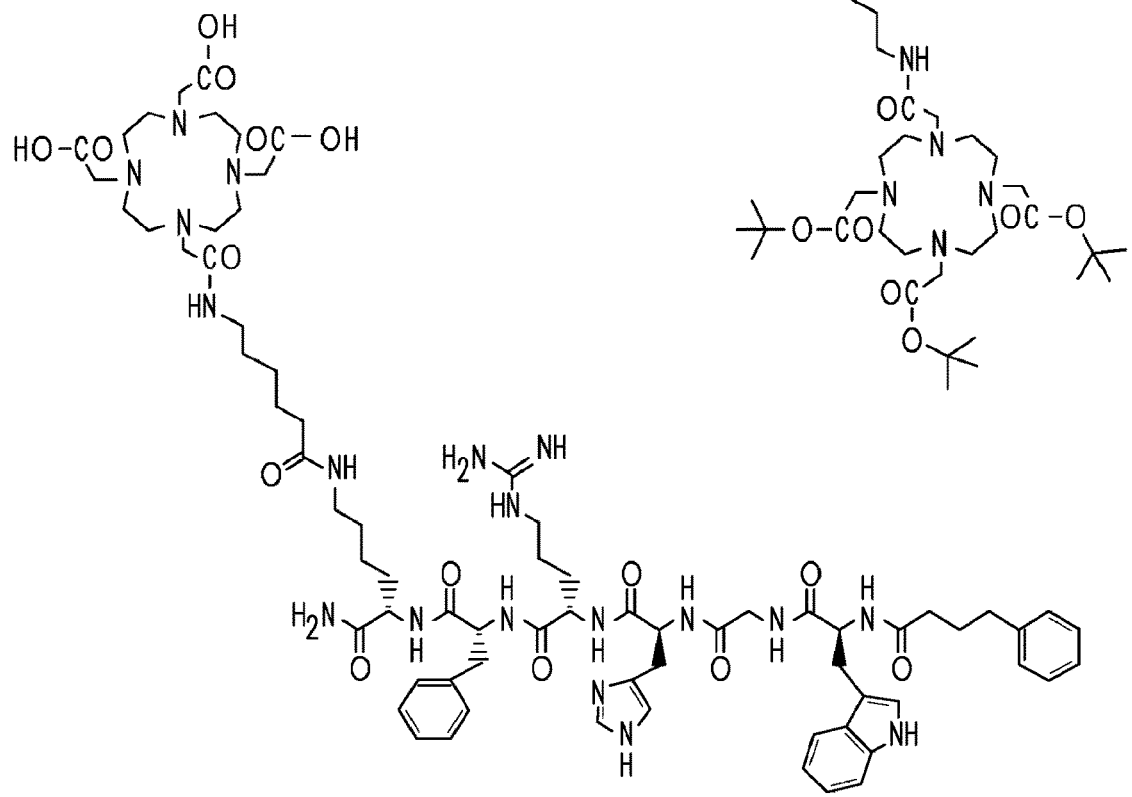

FIG.12

NH₂-Tentagel RAM 1) a) Remove Fmoc, b) Couple 4eq. Fmoc-Lys(alloc)OH, 4eq. HCTU, 8eq. DIEA
2) a) Remove Fmoc, b) Couple 4eq. Fmoc-D-Gly-OH, 4eq. HCTU, 8eq. DIEA
3) a) Remove Fmoc, b) Couple 4eq. Fmoc-Trp(Boc)-OH, 4eq. HCTU, 8eq. DIEA
4) a) Remove Fmoc, b) Couple 4eq. Fmoc-Arg(Pbf)-OH, 4eq. HCTU, 8eq. DIEA
5) a) Remove Fmoc, b) Couple 4eq. Fmoc-D-Phe-OH, 4eq. HCTU, 8eq. DIEA
6) a) Remove Fmoc, b) Couple 4eq. Fmoc-His(Trt)-OH, 4eq. HCTU, 8eq. DIEA
7) a) Remove Fmoc, b) Couple 4eq. 4-phenylbutyric acid, 4eq. HCTU, 8eq. DIEA
8) a) Remove alloc, b) Couple 4eq. DOTA-Trt-t-butyl-ester, 4eq. HCTU, 8eq. DIEA

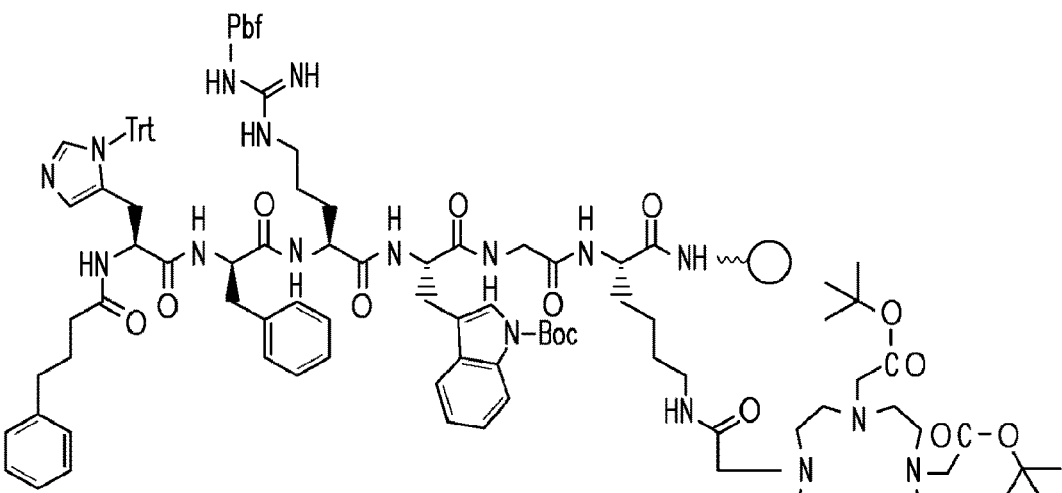

1) Cleavage: TFA, H₂O, Triethysilane
2) Lyophilization
3) HPLC Purification

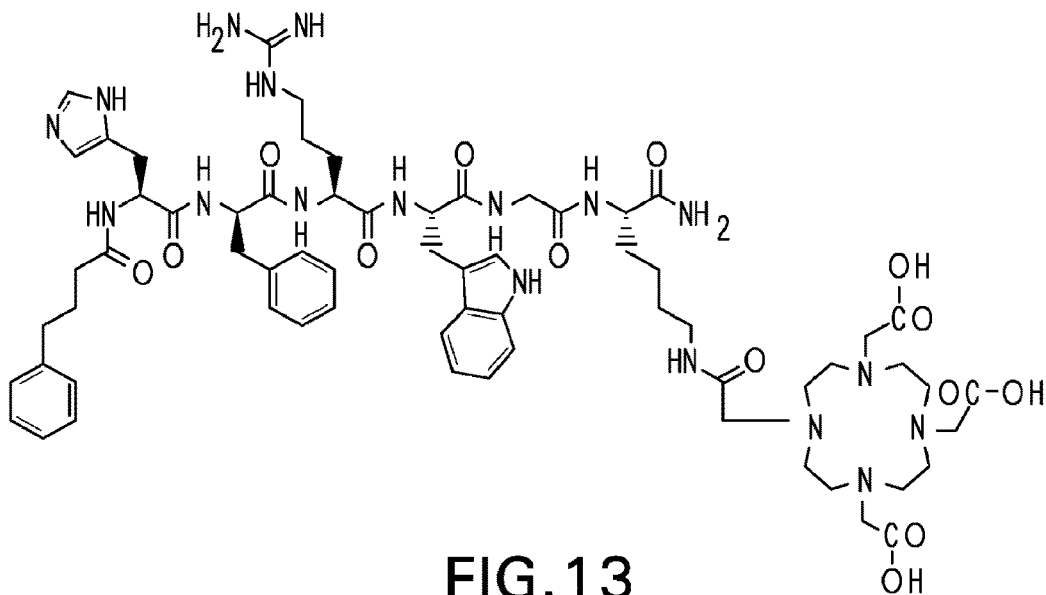

FIG.13

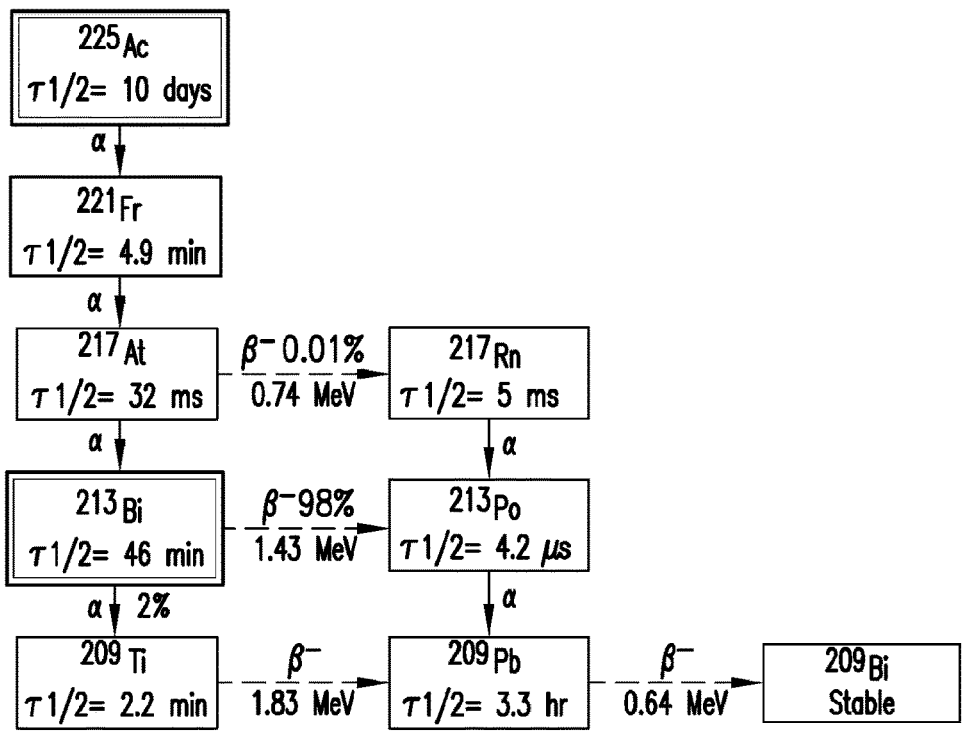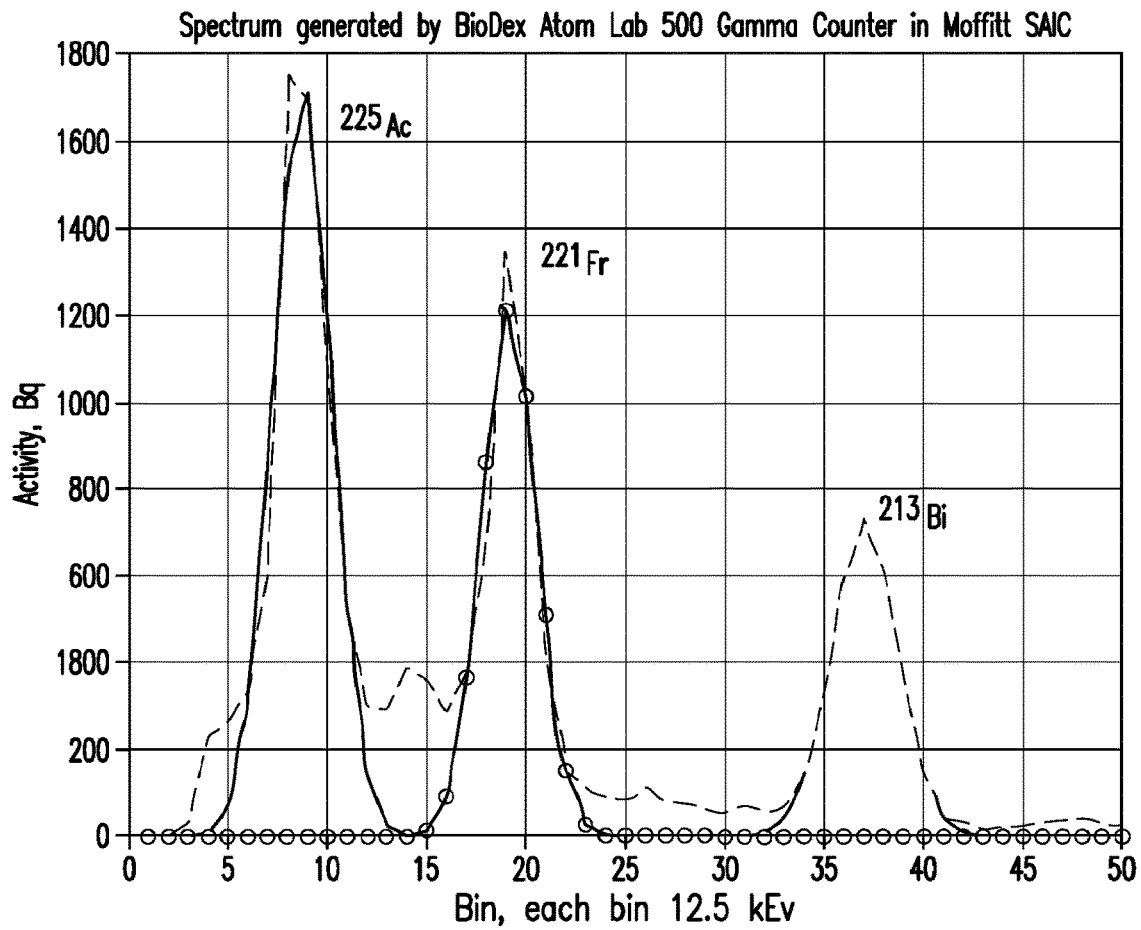
FIG.16

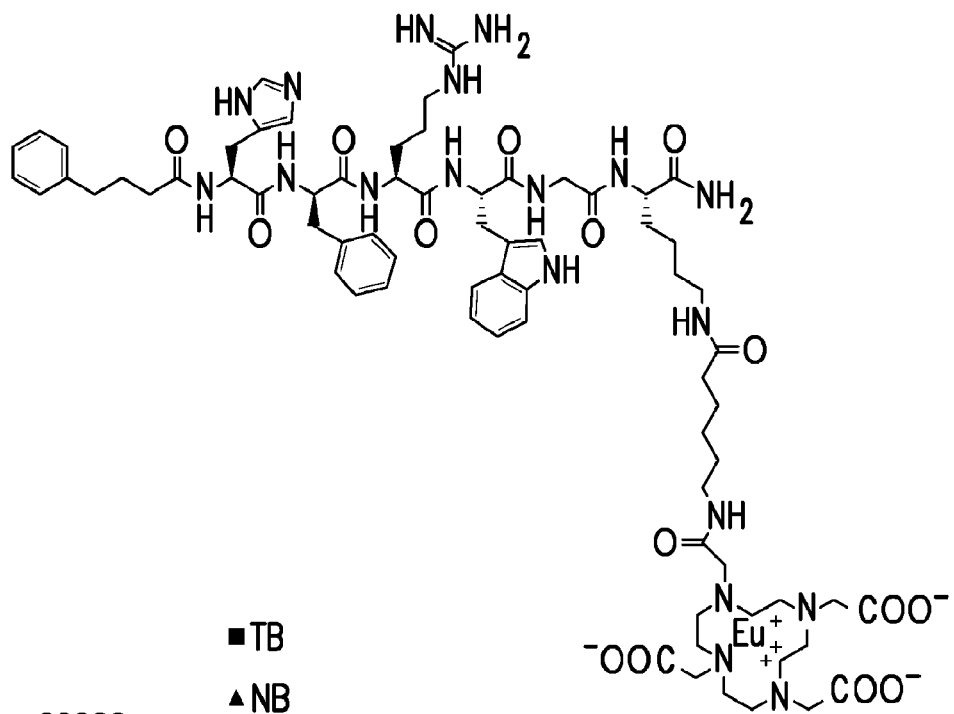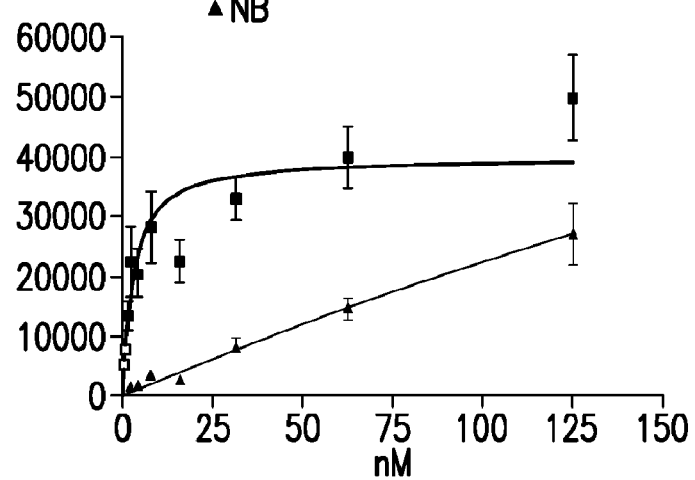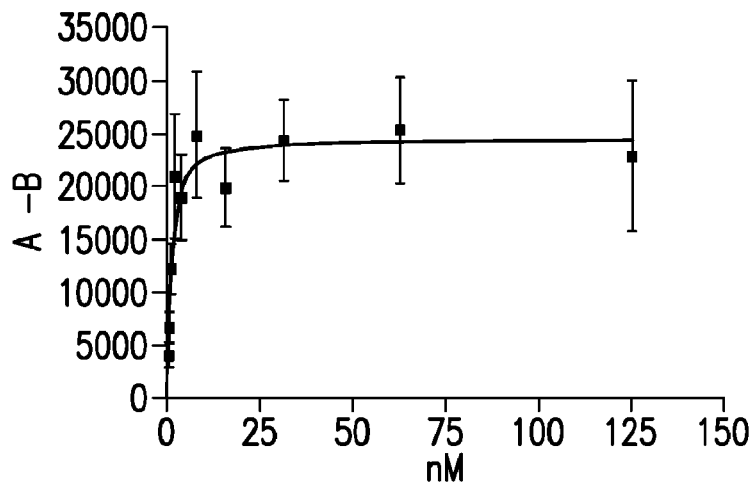
FIG.17

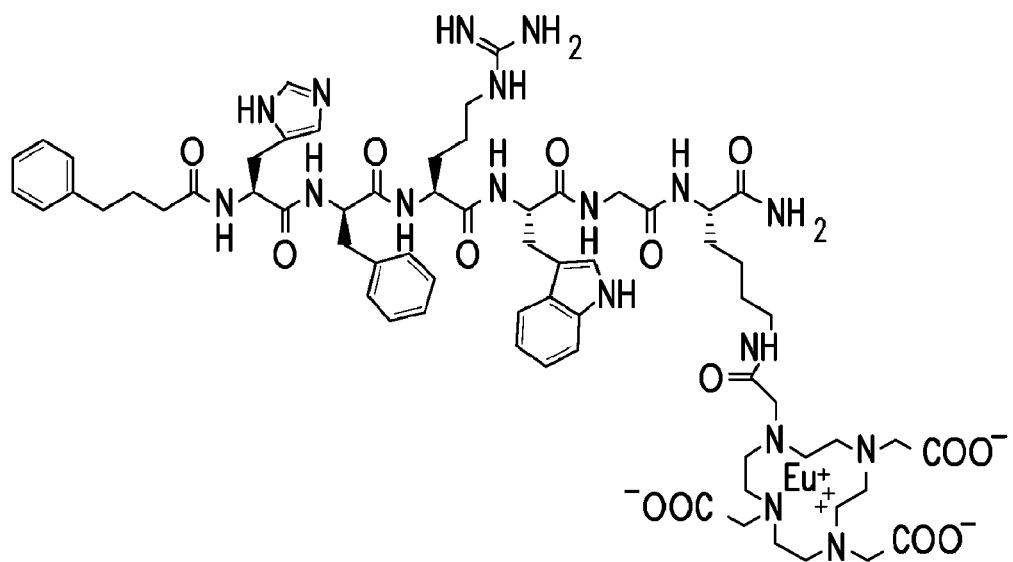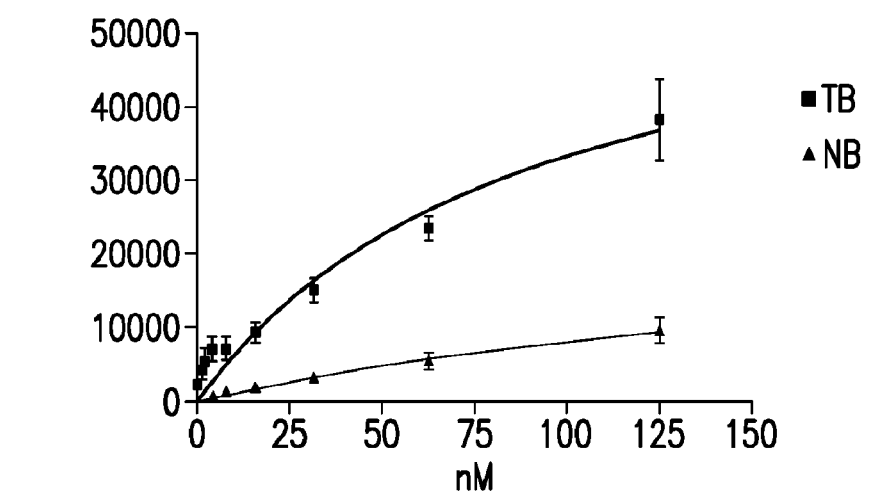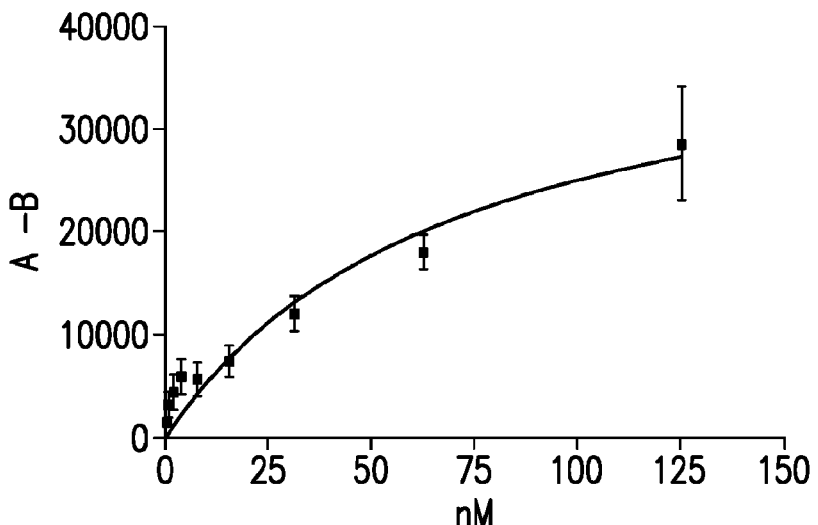
FIG.18

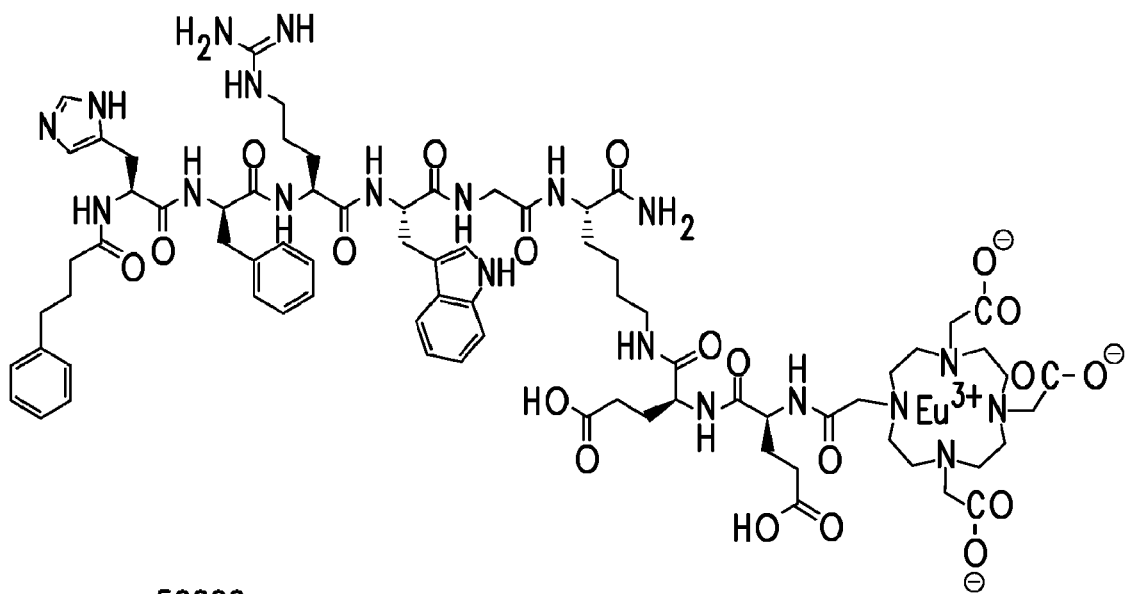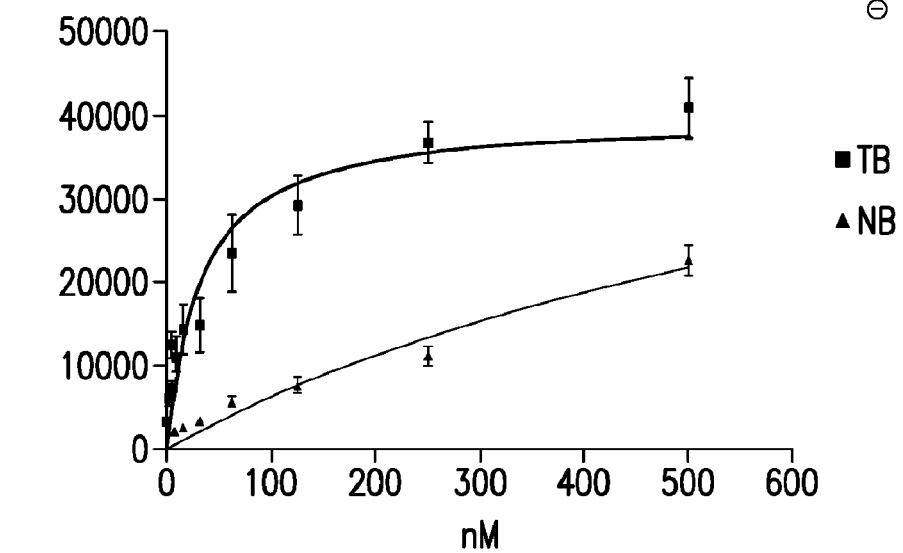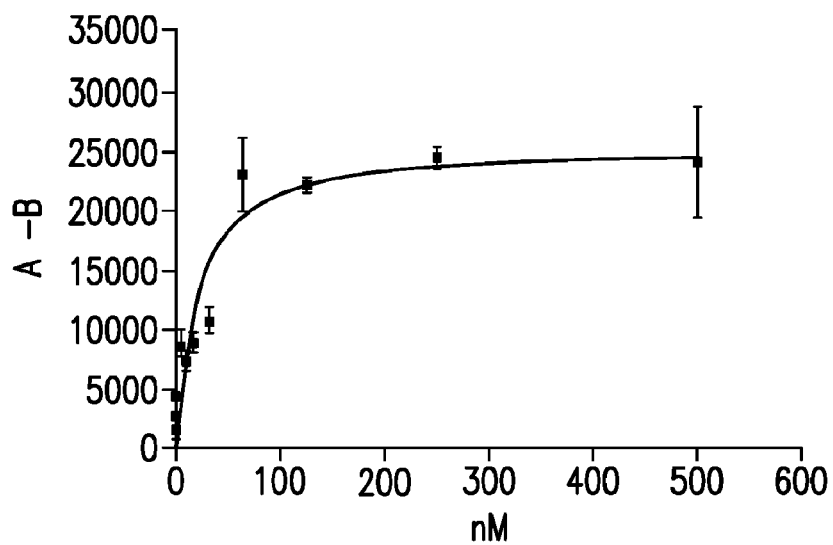
FIG. 19

RADIOTHERAPEUTIC AND COMPANION IMAGING AGENTS TO TARGET MC1R

CROSS REFERENCE TO RELATED APPLICATIONS

This application claims the benefit of priority to U.S. Provisional Application 62/157,784, filed May 6, 2015, which is incorporated by reference herein in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is SEQUENCE_LISTING_670131_402_C1.txt. The text file is 830 bytes, was created on Sep. 18, 2019, and is being submitted electronically via EFS-Web.

FIELD

The subject matter disclosed herein relates generally to targeted radiotherapy with a focus on cancer therapy and anti-cancer compounds and imaging agents. More specifically, the subject matter disclosed herein relates to agents that target MC1R and their use in the treatment of cancer. Methods of screening for MC1R targeted agents are also disclosed.

BACKGROUND

Of all cancers, the incidence of melanoma is the fastest growing worldwide. If discovered early melanoma can be curable by surgical resection, however, the 10 year survival rate of patients with disseminated disease has remained low at 10 to 15%. There have been recent successes with novel therapies in treating patients with advanced disease, for example, the immunotherapetic ipilimumab, which blocks the immune suppressor CTLA-4, and novel targeted therapies such as vemurafenib that inhibits the mutated driver gene BRAF. However, these exciting therapies are effective in only a fraction of patients and targeted inhibitors have the drawback of the rapid development of resistance. Recent work has suggested that by combining targeted therapies, the disease free interval can be increased and that some combinations could even be curative.

Uveal melanoma, the most common ocular malignancy, has a very poor prognosis with a median survival of less than one year when metastatic disease develops (Pereira P R, Odashiro A N, et al., Current and emerging treatment options for uveal melanoma. *Clinical ophthalmology.* 2013, 7:1669-82; Singh A D, et al., Uveal melanoma: trends in incidence, treatment, and survival. *Ophthalmology.* 2011, 118(9):1881-5; Augsburger J J, et al., Effectiveness of treatments for metastatic uveal melanoma. *Am J Ophthalmol.* 2009, 148 (1):119-27). The liver is the most common site of metastasis and liver-directed or systemic treatments have had modest success rates (Bishop K D, et al., Epidemiology and survival outcomes of ocular and mucosal melanomas: a population-based analysis. *Int J Cancer.* 2014, 134(12):2961-71). Novel targeted therapies with low systemic toxicities are needed for metastatic uveal melanoma.

The melanocortin-1 receptor (MC1R) is a bona fide melanoma target. MC1R is a member of a family of five G protein coupled melanocortin receptors, four of which bind melanocyte-stimulating hormone (MSH) and related ligands (MC1R, 3R, 4R & 5R) (Yang Y. Structure, function and regulation of the melanocortin receptors. *Eur J Pharmacol.* 2011, 660(1):125-30). MC3R, 4R and 5R are expressed in tissues of concern (e.g., kidney) (Chhajlani V. Distribution of cDNA for melanocortin receptor subtypes in human tissues. *Biochem Mol Biol Int.* 1996; 38(1):73-80). MC1R is expressed in 94% of uveal melanomas and appears an ideal target (Kiessling R, et al., Melanocortin 1 receptor is expressed by uveal malignant melanoma and can be considered a new target for diagnosis and immunotherapy. *Investigative ophthalmology & visual science.* 2007, 48(3): 1219-27), as it is not expressed in normal tissues of concern in humans (Tafreshi N K, et al., In Vivo and in Silico Pharmacokinetics and Biodistribution of a Melanocortin Receptor 1 Targeted Agent in Preclinical Models of Melanoma. *Mol Pharm.* 2013), but is expressed in the central nervous system and immune cells. However, agents can be easily generated that do not cross the blood brain barrier (BBB) and immune cell depletion is clinically manageable. Hence, a MC1R specific targeting ligand is likely to have tolerable toxicities.

The specificity and affinity (0.24 nM Ki) of MC1RL has been investigated and shown to retain high affinity and biostability following bioconjugation (Barkey N M, et al., Development of melanoma-targeted polymer micelles by conjugation of a melanocortin 1 receptor (MC1R) specific ligand. *J Med Chem.* 2011; 54(23):8078-84). Specifically, a near-infrared fluorescent (NIRF) dye conjugated analog (MC1RL-800) has high binding affinity (0.4±0.1 nM Ki) and in vivo specificity for tumors that express MC1R (Tafreshi N K, et al., Synthesis and characterization of a melanoma-targeted fluorescence imaging probe by conjugation of a melanocortin 1 receptor (MC1R) specific ligand. *Bioconjug Chem.* 2012, 23(12):2451-9). Additionally, PK, BD and tumor cell uptake of MC1RL-800 using in vivo fluorescence tomographic imaging, intravital confocal fluorescence microscopy and a novel mathematical model indicate that MC1RL-800 does not cross the BBB and undergoes rapid renal clearance.

Hence, there is a significant need for new targeted therapeutics with limited side effects that can be used individually or in combination. The compositions and methods disclosed herein address these and other needs.

SUMMARY

In accordance with the purposes of the disclosed materials and methods, as embodied and broadly described herein, the disclosed subject matter, in one aspect, relates to compounds, compositions and methods of making and using compounds and compositions. In specific aspects, the disclosed subject matter relates to cancer therapy and to anti-cancer compounds and imaging agents. More specifically, the subject matter disclosed herein relates to radiopharmaceutical and nuclear medicine agents that target MC1R and their use in the treatment of cancer. Methods of screening for new agents that target MC1R are also disclosed. Also disclosed are PET companion agents and their use with the disclosed compounds.

Additional advantages will be set forth in part in the description that follows or may be learned by practice of the aspects described below. The advantages described below will be realized and attained by elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying figures, which are incorporated in and constitute a part of this specification, illustrate several aspects described below.

FIG. 5 is a schematic of the preparation of compounds as disclosed herein.

FIG. 6A shows average % weight gain, FIG. 6B shows blood urea nitrogen (BUN) level, and FIG. 6C shows blood creatinine levels by groups of animals treated with a range of MC1RL-DOTA-$^{225}$Ac radioactivities.

FIG. 11 is a schematic of the preparation of compounds as disclosed herein.

FIG. 12 is a schematic of the preparation of compounds as disclosed herein.

FIG. 13 is a schematic of the preparation of compounds as disclosed herein.

FIG. 16 shows that gamma spectra are used to calculate dosages and determine radiodosimetry. Decay products of $^{225}$Ac are shown in the top panel. The bottom panel shows the gamma spectrum of $^{225}$Ac and its decay products in a tissue specimen. Data was generated by the BioDex Atom Lab 500 Wipe Test Counter.

FIG. 17, top panel, shows MC1RL linked through aminohexanoic acid (Ahx) to DOTA:$^{152}$Eu. The binding sequence is 1-Phenylbutyric acid-His(D)Phe-Arg-Trp-Gly-Lys(Ahx-DOTA)-CONH$_2$. Eu is chelated into the conjugated DOTA for lanthanide-based binding assays but $^{225}$Ac, $^{68}$Ga, or $^{111}$In can also be chelated. The middle panel shows total and nonspecific saturation binding. 20×MC1Rl-DOTA was used for blocking. The bottom panel shows specific binding, which is the result of subtracting nonspecific binding from total binding. Data is the result of two repeats. $K_d$=0.88 nM; $R^2$=0.42.

FIG. 18, top panel, shows MC1RL linked to DOTA:$^{152}$Eu. The binding sequence is 1-Phenylbutyric acid-His(D)Phe-Arg-Trp-Gly-Lys(DOTA)-CONH$_2$. Eu is chelated into the conjugated DOTA for lanthanide-based binding assays but $^{225}$AC, $^{68}$Ga, or $^{111}$In can also be chelated. The middle panel shows total and nonspecific saturation binding. 20×MC1Rl-DOTA was used for blocking. The bottom panel shows specific binding, which is the result of subtracting nonspecific binding from total binding. Data is the result of two repeats. $K_d$=0.69 nM; $R^2$=0.72.

FIG. 19, top panel, shows MC1RL linked through D-di-Glu to DOTA:$^{152}$Eu. The binding sequence is 1-Phenylbutyric acid-His(D)Phe-Arg-Trp-Gly-Lys(D-di-Glu-DOTA)-CONH$_2$. Eu is chelated into the conjugated DOTA for lanthanide-based binding assays but $^{225}$Ac, $^{68}$Ga, or $^{111}$In can also be chelated. The middle panel shows total and nonspecific saturation binding. 20×MC1Rl-DOTA was used for blocking. The bottom panel shows specific binding, which is the result of subtracting nonspecific binding from total binding. Data is the result of two repeats. $K_d$=0.19 nM; $R^2$=0.78.

Figure 1A:
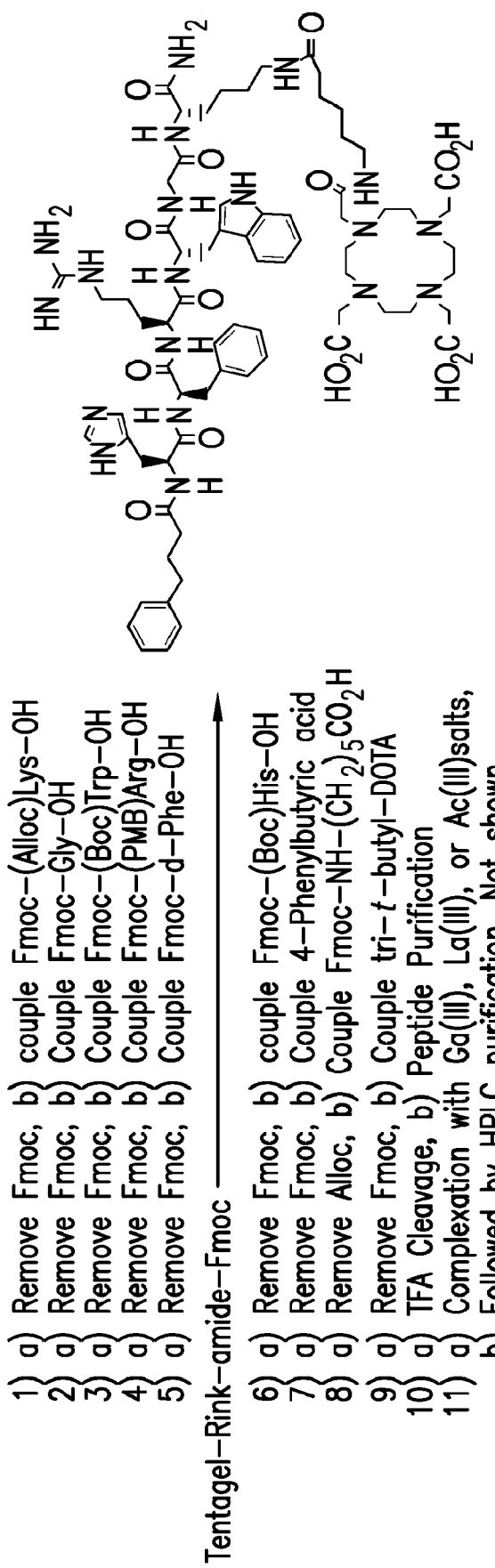
FIG. 1A, shows the synthesis scheme of DOTA-MC1RL $^{225}$Ac-DOTA-MC1RL.

$CONH_2$. Eu is chelated into the conjugated DOTA for lanthanide-based binding assays but $^{225}$Ac, $^{68}$Ga, or $^{111}$In can also be chelated. The middle panel shows total and nonspecific saturation binding. 20×MC1Rl-DOTA was used for blocking. The bottom panel shows specific binding, which is the result of subtracting nonspecific binding from total binding. Data is the result of two repeats.

DETAILED DESCRIPTION

The materials, compounds, compositions, and methods described herein may be understood more readily by reference to the following detailed description of specific aspects of the disclosed subject matter and the Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

In this specification and in the claims that follow, reference will be made to a number of terms, which shall be defined to have the following meanings:

Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an inhibitor" includes mixtures of two or more such inhibitors, reference to "the kinase" includes mixtures of two or more such kinase, and the like.

"Optional" or "optionally" means that the subsequently described event or circumstance can or cannot occur, and that the description includes instances where the event or circumstance occurs and instances where it does not.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used. Further, ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Unless stated otherwise, the term "about" means within 5% (e.g., within 2% or 1%) of the particular value modified by the term "about."

By "reduce" or other forms of the word, such as "reducing" or "reduction," is meant lowering of an event or characteristic (e.g., tumor growth, metastasis). It is understood that this is typically in relation to some standard or expected value, in other words it is relative, but that it is not always necessary for the standard or relative value to be referred to. For example, "reduces tumor growth" means decreasing the amount of tumor cells relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

As used herein, "treatment" refers to obtaining beneficial or desired clinical results. Beneficial or desired clinical results include, but are not limited to, any one or more of: alleviation of one or more symptoms (such as tumor growth or metastasis), diminishment of extent of cancer, stabilized (i.e., not worsening) state of cancer, preventing or delaying spread (e.g., metastasis) of the cancer, preventing or delaying occurrence or recurrence of cancer, delay or slowing of cancer progression, amelioration of the cancer state, and remission (whether partial or total).

The term "patient" preferably refers to a human in need of treatment with an anti-cancer agent or treatment for any purpose, and more preferably a human in need of such a treatment to treat cancer, or a precancerous condition or lesion. However, the term "patient" can also refer to non-human animals, preferably mammals such as dogs, cats, horses, cows, pigs, sheep and non-human primates, among others, that are in need of treatment with an anti-cancer agent or treatment.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

As used herein, the term "composition" is intended to encompass a product comprising the specified ingredients in the specified amounts, as well as any product which results, directly or indirectly, from combination of the specified ingredients in the specified amounts.

References in the specification and concluding claims to parts by weight of a particular element or component in a composition denotes the weight relationship between the element or component and any other elements or components in the composition or article for which a part by weight is expressed. Thus, in a mixture containing 2 parts by weight of component X and 5 parts by weight component Y, X and Y are present at a weight ratio of 2:5, and are present in such ratio regardless of whether additional components are contained in the mixture.

A weight percent (wt. %) of a component, unless specifically stated to the contrary, is based on the total weight of the formulation or composition in which the component is included.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

Compounds

Melanocyte stimulating hormone receptors (MCR) are expressed on surface of melanocytes. MCR is a family of 5 G-protein coupled receptors. MCR are expressed in variety of tissue types: brain/hair/skin (MC1R), kidneys/lung (MC5R), adrenal glands (MC2R), hypothalamus/heart (MC3R/MC4R). Isoform 1 (MC1R) serves as good biomarker of malignant, uveal, and metastatic melanomas. MC1R is expressed as mRNA in 80% of malignant melanomas and 94% of uveal melanomas; it is expressed as protein in 97% of melanoma metastases (highly overexpressed in 50%); and it is expressed in 40% of metastases that aren't candidates for current melanoma targeted therapy. The high cell-surface expression of MC1R makes it a target for both imaging and radiotherapeutics Uveal melanoma is a subtype that has been largely underserved by currently available therapies. The melanocortin 1 receptor (MC1R) is highly expressed in 94% of uveal melanomas, but is generally not expressed in normal tissues of concern for toxicity. For example, MC1R is expressed in the normal central nervous system (CNS), however targeted agents can be constructed that do not cross the blood brain barrier (BBB), and MC1R is expressed in some immune cells, which can be temporarily depleted without significant side effects. By immunohistochemistry (IHC) of patient samples, it has been shown that MC1R is also highly expressed in nearly half of all melanoma metastases. Therefore, novel therapeutic agents that specifically target MC1R have potential for a significant impact in the treatment of late-stage and uveal melanomas. While most targeted therapies have focused on inhibition of pathways that drive the cancer phenotype, there has recently been success in targeted radiotherapy of solid tumors, i.e., the "smart bomb" approach. In fact, an alpha-particle emitting radiotherapeutic agent, a $^{212}$Pb/$^{212}$Bi alloy using the alpha-melanocyte-stimulating hormone (α-MSH) as a targeting scaffold has been developed for melanoma that non-specifically targets the melanocortin family of receptors. However, a problem with this agent is that it is not specific for the MC1R isoform and also targets other family members that are expressed in organs of concern for toxicity, e.g., heart and kidney.

Disclosed herein is a targeting scaffold that is specific for MC1R and have conjugated imaging contrast agents to the scaffold and demonstrated high selectivity for MC1R expressing tumors in vivo and rapid systemic clearance, without retention in tissues of concern for toxicity. The disclosed compounds comprise a targeting sequence for MC1R that comprises the peptide HFRWGK (SEQ ID NO. 1) (MC1R binding sequence). The peptide can be protected at the N and/or C terminus by protecting groups known in the art, e.g., trityl, Fmoc, Boc, benzyl, acetate, 4-phenylbutyryl, Ac-homophenylalanine, and the like. The disclosed compounds also comprise a radionuclide or imaging moiety that is conjugated to the MC1R binding sequence. The radionuclide or imagining moiety can be conjugated to the targeting scaffold by use of the lysine side chain. That is, the amino group in the lysine residue can be bound directly to the radionuclide or imaging moiety or bound to a linker, which is bound to the radionuclide or imaging moiety.

Additional targeting sequences that can be used herein are WGHRFK (SEQ ID NO. 2) which can be protected or unprotected as disclosed herein.

1,4,7,10-tetraazacyclo-dodecane-1,4,7,10-tetraacetic acid (DOTA) was conjugated to the MC1R specific sequence (DOTA-MC1RL) and chelated to the alpha emitting radionuclide $^{225}$Ac and the nonradioactive surrogates $^{139}$La (substitute for $^{225}$Ac), and $^{67/69}$Ga (substitute for $^{68}$Ga positron emission tomography radionuclide); it demonstrated high binding affinity (0.3 nM $K_i$), 97% radiosynthesis yield, 98% purity and >90% biostability after 10 days in plasma at 37° C.

Targeted treatment of metastatic melanoma can be informed by use of a companion PET imaging agent and that patients with avidity for the PET agent can be successfully treated with the corresponding targeted therapy. MC1RL targeted radiotherapeutic with a companion targeted PET imaging agent are disclosed.

In specific aspects disclosed are compounds having Formula I.

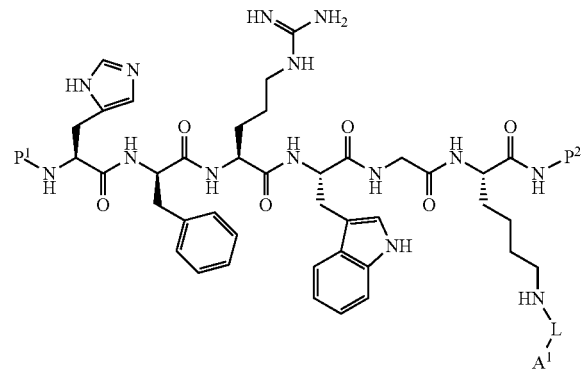

wherein $P^1$ and $P^2$ are independently H or amine protecting groups or one or more additional amino acids selected from the group consisting of alanine, valine, leucine, isoleucine, proline, histidine, methionine, methionine sulfoxide, phenylalanine, serine, threonine, phenylglycine, norleucine, norvaline, alpha-aminobutyric acid, O-methylserine, O-ethylserine, S-methylcysteine, S-ethylcysteine, S-benzylcysteine, $NH_2$—$CH(CH_2CHEt_2)$-COOH, alpha-aminoheptanoic acid, $NH_2$—$CH(CH_2$-cyclohexyl)-COOH, $NH_2$—$CH(CH_2$-cyclopentyl)-COOH, $NH_2$—$CH(CH_2$-cyclobutyl)-COOH, $NH_2$—$CH(CH_2$-cyclopropyl)-COOH, 5,5,5-trifluoroleucine, α-aminohexanoic acid, thiaproline, and hexafluoroleucine;

L is an optional linking moiety of from 1 to 30 carbon atoms in length; and $A^1$ is a radionuclide chelating moiety;

or an ionized derivative thereof.

Additional examples of protecting groups are trityl, Fmoc, Boc, benzyl, acetate, 4-phenylbutyryl, Ac-homophenylalanine, and the like. In specific examples, $P^1$ is 4-phenylbutyryl. In other examples, $P^2$ is H.

The compounds described herein can contain a linker (L) that connects the radionuclide chelating moiety to the lysine residue of the MC1R binding sequence. Alternatively, the linker can be absent and the radionuclide chelating moiety is bound directly to the lysine residue of the MC1R binding sequence. The term "linker", as used herein, refers to one or more polyfunctional, e.g., bi-functional or tri-functional molecules, which can be used to covalently couple the chelating moieties to the MC1R binding sequence. The linker can be attached to any part of the MC1R binding sequence so long as the point of attachment does not interfere with the biological activity, for example, the antitumor activity of the compounds described herein.

The linker can be a single atom, such as a heteroatom (e.g., O, N, or S), a group of atoms, such as a functional group (e.g., amine, —C(=O)—, —$CH_2$—), or multiple groups of atoms, such as an alkylene chain. Suitable linkers include but are not limited to oxygen, sulfur, carbon, nitrogen, alkyl, cycloalkyl, cycloalkenyl, heterocycloalkyl, alkoxyl, aryl, heteroaryl, ether, amine, diamine, amide, alkylamine, thioether, carboxylates, polymer, derivatives or combinations thereof.

The linker can be $R^{14}$, $C(O)R^{14}C(O)$, $C(O)OR^{14}OC(O)$, $C(O)R^{14}N$, $C(O)OR^{14}NH$, $NHR^{14}NH$, or $C(O)NHR^{14}NHC(O)$, $C(S)OR^{14}OC(S)$; wherein $R^{14}$ is O, S, $C_1$-$C_{20}$ alkyl; $C_1$-$C_{20}$ heteroalkyl; $C_1$-$C_{20}$ alkylamine; $C_1$-$C_{20}$ alkoxyl; $C_1$-$C_{20}$ alkanoyloxyl; or $C_1$-$C_{20}$ alkylamido, any of which can optionally be substituted with one or more substituents including halogen, alkoxyl, alkyl, alkenyl, cycloalkyl, cycloalkenyl, heterocycloalkyl, aryl, heteroaryl, amine, cyano, nitro, hydroxyl, carbonyl, acyl, carboxylic acid (—COOH), —$C(O)R^{12}$, —$C(O)OR^{12}$, carboxylate (—COO$^-$), primary amide (e.g., —$CONH_2$), secondary amide (e.g., —$CONHR^{12}$), —$C(O)NR^{12}R^{13}$, —$NR^{12}R^{13}$, —$NR^{12}S(O)_2R^{13}$, —$NR^{12}C(O)R^{13}$, —$S(O)_2R^{12}$, —$SR^{12}$, and —$S(O)_2NR^{12}R^{13}$, sulfinyl group (e.g., —$SOR^{12}$), and sulfonyl group (e.g., —$SOOR^{12}$); wherein $R^{12}$ and $R^{13}$ can each independently be hydrogen, halogen, hydroxyl, alkyl, haloalkyl, alkenyl, alkynyl, cycloalkyl, heterocycloalkyl, aryl, heteroaryl, carbonyl, cyano, amino, alkylamino, dialkylamino, alkoxyl, aryloxyl, cycloalkyl, alkoxycarbonyl, aminocarbonyl, alkylaminocarbonyl, or dialkylaminocarbonyl.

In some embodiments, the linker is $NR^{14}R^{15}R^{16}$ or $(CH)R^{14}R^{15}R^{16}$; wherein the MC1R binding moiety or detectable moiety are bonded to at least one of $R^{14}R^{15}R^{16}$, and wherein $R^{14}$, $R^{15}$, and $R^{16}$ are each independently hydrogen, $C_1$-$C_{20}$ alkyl; $C_1$-$C_{20}$ heteroalkyl; $C_1$-$C_{20}$ alkylamine; $C_1$-$C_{20}$ alkoxy; $C_1$-$C_{20}$ alkanoyloxy; or $C_1$-$C_{20}$ alkylamido; any of which can be optionally substituted with one or more substituents independently selected from the group consisting of halogen; hydroxyl; cyano; nitro; amino; alkylamino; dialkylamino; amido; alkylamido; =O; —$S(O)_2$; —SO—; —S—; —$S(O)_2N$—; haloalkyl; hydroxyalkyl; carboxy; alkoxy; aryloxy; alkoxycarbonyl; aminocarbonyl; alkylaminocarbonyl; and dialkylaminocarbonyl. For example, the linker is —$(C(O)R^{14})_3N$, —$(R^{14})_3N$, —$(S(O)_2R^{14})_3N$, —$(C(O)R^{14})_3CH$, —$(R^{14})_3CH$, or —$(S(O)_2R^{14})_3CH$. In some embodiments, $C_{1-20}$ refers to alkyl groups containing 1, 2, 3, 4, 5, 6, 7, 8, 9, 10, 11, 12, 13, 14, 15, 16, 17, 18, 19, or 20 carbons. In some embodiments, the linker is —$(CO-R^{14})_2NH$, —$(R^{14})_2NH$, —$(SO_2R^{14})_2NH$, —$(SOR^{14})_2NH$, —$(OR^{14})_2NH$, —$(O-CO-R^{14})_2NH$, —$(CO-O-R^{14})_2NH$, —$(CO-R^{14})_2CH_2$, —$(R^{14})_2CH_2$, —$(SO_2R^{14})_2CH_2$, —$(SOR^{14})_2CH_2$, —$(O-CO-R^{14})_2CH_2$, or —$(OR^{14})_2CH_2$. Suitable examples of linkers are $C(O)NH(CH_2)_n$—, where n is from 1 to 20, or $C(O)(CH_2O)_n$, where n is from 1 to 10.

The radionuclide binding moiety $A^1$ can be any cyclic or acyclic moiety that will chelate a radionuclide. A specific example of a suitable radionuclide binding moieties is DOTA (1,4,7,10-Tetraazacyclododecane-1,4,7,10-tetraacetic acid) as the chelating moiety, other chelating moieties can be attached at the lysine side chain of the MC1R binding sequence, such as DTPA (diethylene triamine pentaacetic acid), DOTP (1,4,7,10-Tetraazacyclododecane-1,4,7,10-tetra(methylene phosphonic) acid), DOTMA, (1R,4R,7R,10R)-α'α"α'''-Tetramethyl-1,4,7,10-tetraazacyclododecane-1,4,7,10-tetraacetic acid) tetrasodium salt, TETA, (1,4,8,11-Tetraazacyclotetradecane-1,4,8,11-tetraacetic acid), DOTAM (1,4,7,10-Tetrakis(carbamoylmethyl)-1,4,7,10-tetraazacyclododecane), CB-TE2A (1,4,8,11-tetraazabicyclo[6.6.2]hexadecane-4,11-dicetic acid), and NOTA ((1,4,7-triazacyclononane-N,N',N''-triacetic acid).

In specific examples, disclosed are compounds having Formula IA
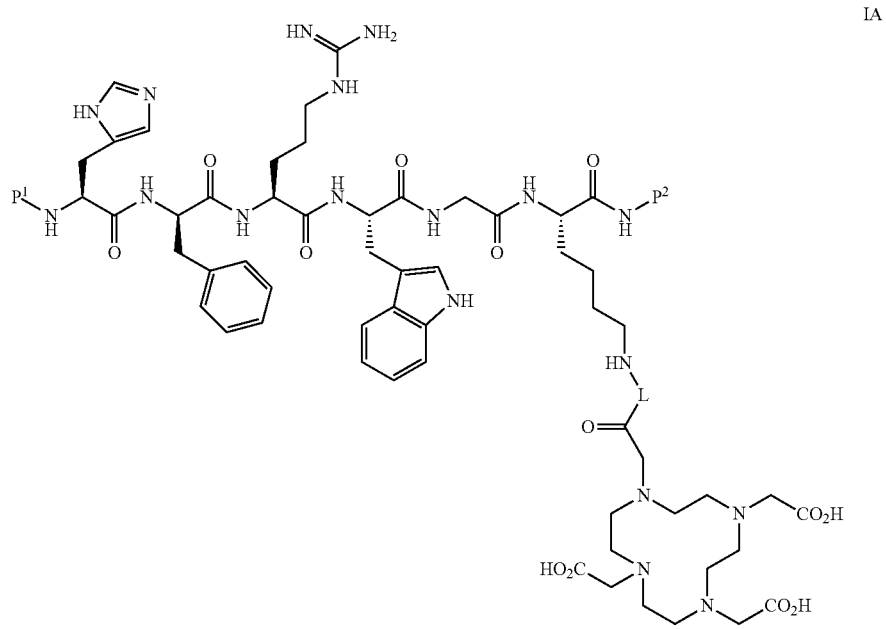
wherein $P^1$, $P^2$, L are as defined herein.
Additional examples of compounds disclosed herein are:
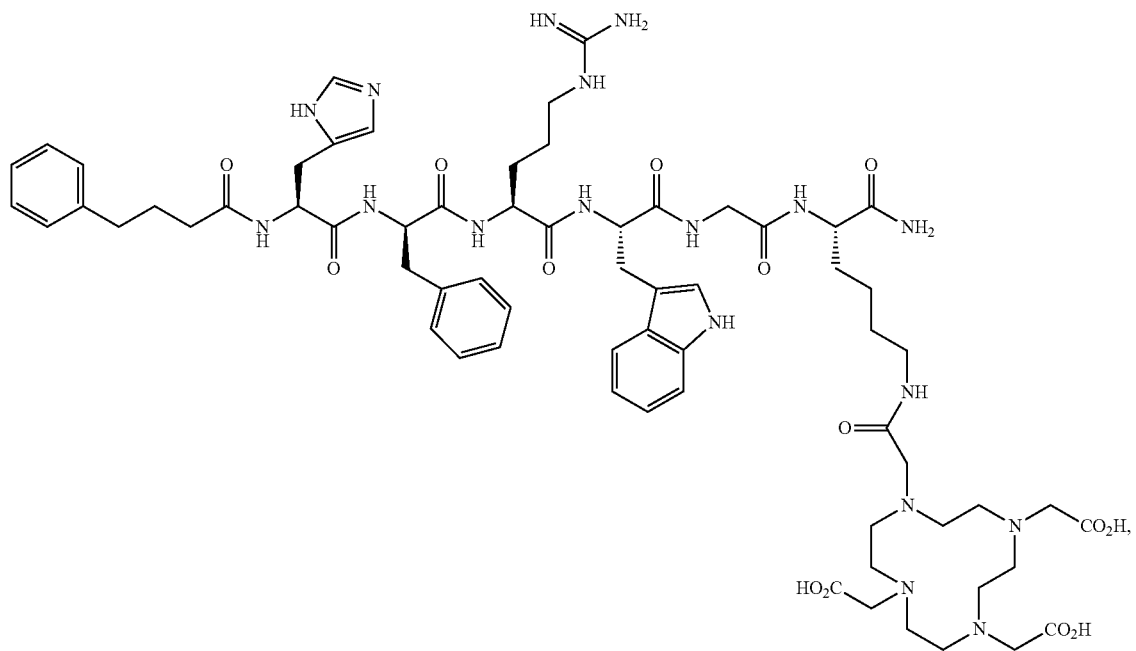

-continued

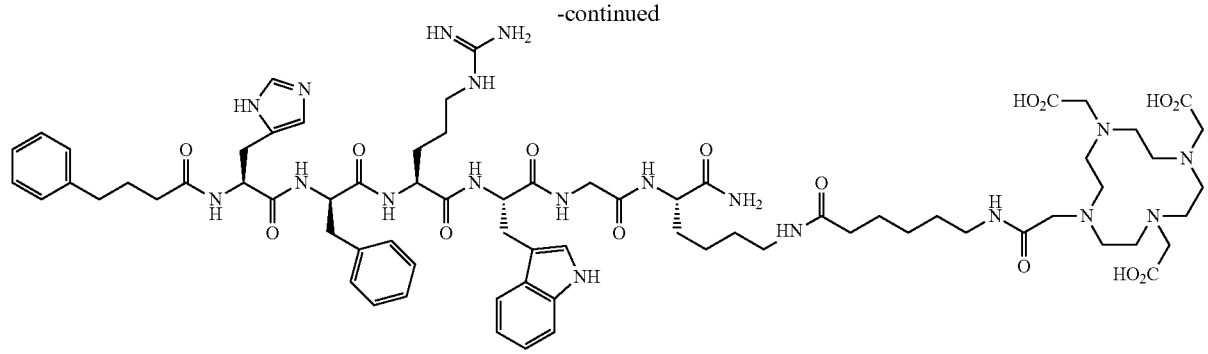

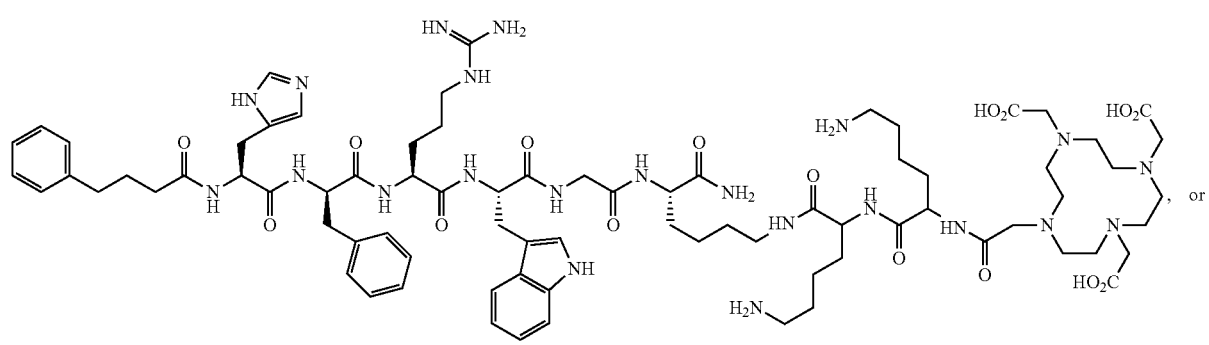

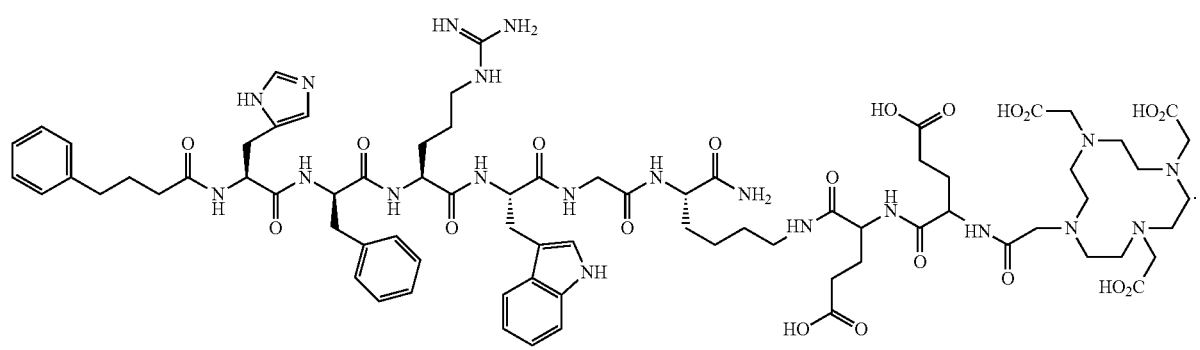

Ionized derivatives of the disclosed compounds are also disclosed. Ionized derivatives are compounds that are protonated or deprotonated and salts thereof.

Also disclosed are any of the compounds disclosed here chelated to a radionuclide. The radionuclide can be an alpha-particle or beta-particle emitter. Relative to β-particles, α-particles minimize collateral damage and are less susceptible to radioresistance. α-particles have a very high linear energy transfer (deposit high energy into surrounding cells), i.e., more efficient cell killing for solid tumors (only 1 to 10 α particle hits per cell vs. thousands of β particles per cell are needed for cell killing). They also travel a very short path (a few cell diameters) so they reduce damage to surrounding nearby normal tissues. However, this is a potential solution to intratumoral heterogeneity of target expression, i.e., adjacent cells can be killed regardless of target expression. For example, compounds of Formula I or the specific compounds disclosed herein can be chelated to $^{90}$Y, $^{177}$Lu, $^{18}$F, $^{64}$Cu, $^{67}$Cu, $^{89}$Zr, $^{124}$I, $^{123}$I, $^{152}$Eu and $^{99m}$Tc. In specific examples, the radionuclide that is chelated to the disclosed compounds is $^{225}$Ac, $^{68}$Ga, or $^{111}$In.

Also disclosed are compounds of Formula II

II

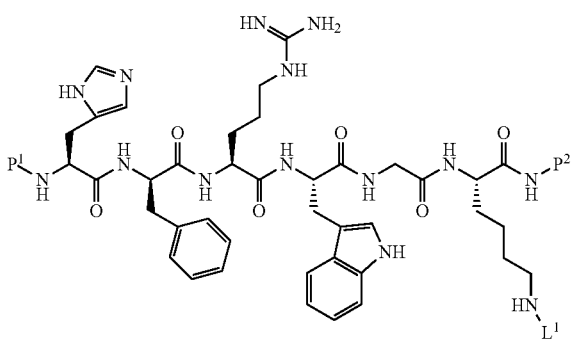

wherein $P^1$ and $P^2$ are as defined above and $L^1$ is a reactive linking moiety. Any of the disclosed linking moieties disclosed above having an additional OH, NH$_2$, SH, N$_3$, or

Method

Further provided herein are methods of treating or preventing cancer in a subject, comprising administering to the subject an effective amount of a compound or composition as disclosed herein. The methods can further comprise administering a second compound or composition, such as, for example, anticancer agents or anti-inflammatory agents. Additionally, the method can further comprise administering an effective amount of ionizing radiation to the subject.

Methods of killing a tumor cell are also provided herein. The methods comprise contacting a tumor cell with an effective amount of a compound or composition as disclosed herein. The methods can further include administering a second compound or composition (e.g., an anticancer agent or an anti-inflammatory agent) and/or administering an effective amount of ionizing radiation to the subject.

Also provided herein are methods of radiotherapy of tumors, comprising administering to a subject a composition as disclosed herein, which delivers ionizing radiation to the tumor.

Also disclosed are methods for treating oncological disorders in a patient. In one embodiment, an effective amount of one or more compounds or compositions disclosed herein is administered to a patient having an oncological disorder and who is in need of treatment thereof. The disclosed methods can optionally include identifying a patient who is or can be in need of treatment of an oncological disorder. The patient can be a human or other mammal, such as a primate (monkey, chimpanzee, ape, etc.), dog, cat, cow, pig, or horse, or other animals having an oncological disorder. Oncological disorders specifically treatable by the disclosed compounds are those that express MC1R, such a melanomas. Still other examples include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma.

Other examples of cancers that can be treated according to the methods disclosed herein are adrenocortical carcinoma, adrenocortical carcinoma, cerebellar astrocytoma, basal cell carcinoma, bile duct cancer, bladder cancer, bone cancer, brain tumor, breast cancer, Burkitt's lymphoma, carcinoid tumor, central nervous system lymphoma, cervical cancer, chronic myeloproliferative disorders, colon cancer, cutaneous T-cell lymphoma, endometrial cancer, ependymoma, esophageal cancer, gallbladder cancer, gastric (stomach) cancer, gastrointestinal carcinoid tumor, germ cell tumor, glioma, hairy cell leukemia, head and neck cancer, hepatocellular (liver) cancer, hypopharyngeal cancer, hypothalamic and visual pathway glioma, intraocular melanoma, retinoblastoma, islet cell carcinoma (endocrine pancreas), laryngeal cancer, lip and oral cavity cancer, liver cancer, medulloblastoma, Merkel cell carcinoma, squamous neck cancer with occult mycosis fungoides, myelodysplastic syndromes, myelogenous leukemia, nasal cavity and paranasal sinus cancer, nasopharyngeal cancer, neuroblastoma, non-small cell lungcancer, oral cancer, oropharyngeal cancer, osteosarcoma, ovarian cancer, pancreatic cancer, paranasal sinus and nasal cavity cancer, parathyroid cancer, penile cancer, pheochromocytoma, pineoblastoma and supratentorial primitive neuroectodermal tumor, pituitary tumor, plasma cell neoplasm/multiple myeloma, pleuropulmonary blastoma, prostate cancer, rectal cancer, renal cell (kidney) cancer, retinoblastoma, rhabdomyosarcoma, salivary gland cancer, Ewing's sarcoma, soft tissue sarcoma, Sezary syndrome, skin cancer, small cell lung cancer, small intestine cancer, supratentorial primitive neuroectodermal tumors, testicular cancer, thymic carcinoma, thymoma, thyroid cancer, transitional cell cancer of the renal pelvis and ureter, trophoblastic tumor, urethral cancer, uterine cancer, vaginal cancer, vulvar cancer, Waldenström's macroglobulinemia, and Wilms' tumor.

In some aspect, disclosed are methods for treating a tumor or tumor metastases in a subject by the administration to the subject a combination of at least one compound or composition as disclosed herein and at least one cancer immunotherapeutic agent. The disclosed compounds can be administered alone or in combination with a cancer immunotherapeutic agent. The subject can receive the therapeutic compositions prior to, during or after surgical intervention to remove all or part of a tumor. Administration may be accomplished via direct immersion; systemic or localized intravenous (i.v.), intraperitoneal (i.p.), subcutaneous (s.c.), intramuscular (i.m.), or direct injection into a tumor mass; and/or by oral administration of the appropriate formulations.

A cancer immunotherapeutic agent suitable for use in the methods disclosed herein is an immunotherapeutic agent which comprises a cell effector component joined to a tumor associated antigen targeting component. Suitable cell effector components can include cytotoxic chemicals, cytotoxic radioisotopes, and cell signaling agents such as cytokines. Suitable tumor targeting components are polypeptide chains which bind to tumor associated antigens present on or in the surrounding tissue matrix of a tumor cell such as receptor protein chains or immunoglobulin chains.

Tumor associated antigens which can be used for targets of the immunotherapeutic agents include a tumor associated antigen selected from the group consisting of AFP, CA 125, CEA, CD19, CD20, CD44, CD45, EGF Receptor, GD[2], GD[3], GM1, GM2, Her-2/Neu, Ep-CAM (KSA), IL-2 receptor, Lewis-Y, Lewis-X (CD 15), melanoma-associated proteoglycan MCSP, PSA and Transferrin Receptor.

Examples of immunotherapeutic agents have an effector component that is a cytokine polypeptide joined to a targeting component which is an immunoglobulin (Ig) polypeptide chain. The Ig polypeptide chain comprises a variable region which binds to a tumor associated antigen. It is preferred that said immunoglobulin chain, when combined with the appropriate complementary chain (i.e. a heavy chain complements a light chain) defines an antibody active site which is specific for a tumor associated antigen.

The tumor targeting Ig portion of the immunotherapeutic agent can comprise an entire immunoglobulin chain amino acid sequence, or at least the fragment of which comprises the antigen binding specificity portion of the protein. Thus, a suitable Ig polypeptide chain will have at least an Ig variable region specific for a tumor associated antigen.

An antibody and polypeptide chains therefrom, suitable for use in the disclosed methods, will have an amino acid sequence that can be of any mammalian origin. Where such antibody protein is not of the same origin as the anticipated patient, fragments of the antibody protein, such as F(ab')2, Fab, Fv or engineered Fv single chain antibody protein can be used. To further reduce antigenicity of the antibody protein, modification of the antibody amino acid sequence may be accomplished to reduce such by making the protein appear more like the patients normal antibody components. For example, monoclonal murine antibody amino acid sequences can be modified to appear more human, for administration to human patients by a variety of processes for humanization of the antibody.

Specific examples of cancer immunotherapeutic agents include an antibody that specifically binds CLTA-4, such as ipilimumab (Bristol-Myers Squibb), anti-PD-1, and anti-PDL1. Other immunotherapeutic agents include the TNFα antagonists (e.g. etanercept), the B cell depleting agent rituximab, the anti-IL-6 receptor tocilizumab, and the costimulation blocker abatacept can be administered with the compounds or compositions disclosed herein.

The disclosed compounds can also be administered with toll like receptor (TLR) agonist. TLR agonist is a ligand for a TLR selected from the group consisting of TLR1, TLR2, TLR3, TLR4, and TLR9. For example, the TLR agonist can be a ligand selected from the group consisting of Pam3CSK4, Pam3CSK4, poly I:C, Ribomunyl, and CpG ODN.

The disclosed compounds can also be administered with an angiogenesis inhibiting agent, which is one which can inhibit the formation of new blood vessels (neovascularization) or enlargement of existing capillary networks into the tissues near a tumor cell. Suitable angiogenesis inhibiting agents can be peptides with angiogenesis inhibiting activity, such as the tumor associated antigen PSA. Other suitable angiogenesis inhibiting agents can be antagonists of VEGF associated angiogenesis, for example antagonists of the VEGF receptor on the surface of cells. One monoclonal antibody which can be used is LM609 (ATCC HB 9537).

Administration

The disclosed compounds can be administered either sequentially or simultaneously in separate or combined pharmaceutical formulations. When one or more of the disclosed compounds is used in combination with a second therapeutic agent, the dose of each compound can be either the same as or differ from that when the compound is used alone. Appropriate doses will be readily appreciated by those skilled in the art.

The term "administration" and variants thereof (e.g., "administering" a compound) in reference to a compound as described herein means introducing the compound or a prodrug of the compound into the system of the animal in need of treatment. When a compound as described herein or prodrug thereof is provided in combination with one or more other active agents (e.g., a cytotoxic agent, etc.), "administration" and its variants are each understood to include concurrent and sequential introduction of the compound or prodrug thereof and other agents.

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, Remington's Pharmaceutical Science by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 99%, and especially, 1 and 15% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 2003/0032594 and 2002/0120100 disclose amino acid sequences that can be coupled to another composition and that allows the composition to be translocated across biological membranes. U.S. Application Publication No. 2002/0035243 also describes compositions for transporting biological moieties across cell membranes for intracellular delivery. Compounds can also be incorporated into polymers, examples of which include poly (D-L lactide-coglycolide) polymer for intracranial tumors; poly[bis(p-carboxyphenoxy) propane:sebacic acid] in a 20:80 molar ratio (as used in GLIADEL); chondroitin; chitin; and chitosan.

For the treatment of oncological disorders, the compounds disclosed herein can be administered to a patient in need of treatment in combination with other antitumor or anticancer substances and/or with radiation and/or photodynamic therapy and/or with surgical treatment to remove a tumor. These other substances or treatments can be given at the same as or at different times from the compounds disclosed herein. For example, the compounds disclosed herein can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively.

Many tumors and cancers have viral genome present in the tumor or cancer cells. For example, Epstein-Barr Virus (EBV) is associated with a number of mammalian malignancies. The compounds disclosed herein can also be used alone or in combination with anticancer or antiviral agents, such as ganciclovir, azidothymidine (AZT), lamivudine (3TC), etc., to treat patients infected with a virus that can cause cellular transformation and/or to treat patients having a tumor or cancer that is associated with the presence of viral genome in the cells. The compounds disclosed herein can also be used in combination with viral based treatments of oncologic disease. For example, the compounds can be used with mutant herpes simplex virus in the treatment of non-small cell lung cancer (Toyoizumi, et al., "Combined therapy with chemotherapeutic agents and herpes simplex virus type IICP34.5 mutant (HSV-1716) in human non-small cell lung cancer," Human Gene Therapy, 1999, 10(18):17).

Therapeutic application of compounds and/or compositions containing them can be accomplished by any suitable therapeutic method and technique presently or prospectively known to those skilled in the art. Further, compounds and compositions disclosed herein have use as starting materials or intermediates for the preparation of other useful compounds and compositions.

Compounds and compositions disclosed herein can be locally administered at one or more anatomical sites, such as sites of unwanted cell growth (such as a tumor site or benign skin growth, e.g., injected or topically applied to the tumor or skin growth), optionally in combination with a pharmaceutically acceptable carrier such as an inert diluent. Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts, hydrates, or analogs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid, and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer them topically to the skin as compositions, in combination with a dermatologically acceptable carrier, which can be a solid or a liquid. Compounds and agents and compositions disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like. Drug delivery systems for delivery of pharmacological substances to dermal lesions can also be used, such as that described in U.S. Pat. No. 5,167,649.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver a compound to the skin are disclosed in U.S. Pat. Nos. 4,608,392; 4,992,478; 4,559,157; and 4,820,508.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art; for example, see U.S. Pat. No. 4,938,949.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

For the treatment of oncological disorders, compounds and agents and compositions disclosed herein can be administered to a patient in need of treatment prior to, subsequent to, or in combination with other antitumor or anticancer agents or substances (e.g., chemotherapeutic agents, immunotherapeutic agents, radiotherapeutic agents, cytotoxic agents, etc.) and/or with radiation therapy and/or with surgical treatment to remove a tumor. For example, compounds and agents and compositions disclosed herein can be used in methods of treating cancer wherein the patient is to be treated or is or has been treated with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation; East Hanover, N.J.) and HERCEPTIN (Genentech, Inc.; South San Francisco, Calif.), respectively. These other substances or radiation treatments can be given at the same as or at different times from the compounds disclosed herein. Examples of other suitable chemotherapeutic agents include, but are not limited to, altretamine, bleomycin, bortezomib (VELCADE), busulphan, calcium folinate, capecitabine, carboplatin, carmustine, chlorambucil, cisplatin, cladribine, crisantaspase, cyclophosphamide, cytarabine, dacarbazine, dactinomycin, daunorubicin, docetaxel, doxorubicin, epirubicin, etoposide, fludarabine, fluorouracil, gefitinib (IRESSA), gemcitabine, hydroxyurea, idarubicin, ifosfamide, imatinib (GLEEVEC), irinotecan, liposomal doxorubicin, lomustine, melphalan, mercaptopurine, methotrexate, mitomycin, mitoxantrone, oxaliplatin, paclitaxel, pentostatin, procarbazine, raltitrexed, streptozocin, tegafur-uracil, temozolomide, thiotepa, tioguanine/thioguanine, topotecan, treosulfan, vinblastine, vincristine, vindesine, vinorelbine. In an exemplified embodiment, the chemotherapeutic agent is melphalan. Examples of suitable immunotherapeutic agents include, but are not limited to, alemtuzumab, cetuximab (ERBITUX), gemtuzumab, iodine 131 tositumomab, rituximab, trastuzamab (HERCEPTIN). Cytotoxic agents include, for example, radioactive isotopes (e.g., I131, I125, Y90, P32, etc.), and toxins of bacterial, fungal, plant, or animal origin (e.g., ricin, botulinum toxin, anthrax toxin, aflatoxin, jellyfish venoms (e.g., box jellyfish, etc.) Also disclosed are methods for treating an oncological disorder comprising administering an effective amount of a compound and/or agent disclosed herein prior to, subsequent to, and/or in combination with administration of a chemotherapeutic agent, an immunotherapeutic agent, a radiotherapeutic agent, or radiotherapy.

Kits

Kits for practicing the methods described herein are further provided. By "kit" is intended any manufacture (e.g., a package or a container) comprising at least one reagent, e.g., anyone of the compounds described herein. The kit can be promoted, distributed, or sold as a unit for performing the methods described herein. Additionally, the kits can contain a package insert describing the kit and methods for its use. Any or all of the kit reagents can be provided within containers that protect them from the external environment, such as in sealed containers or pouches.

To provide for the administration of such dosages for the desired therapeutic treatment, in some embodiments, pharmaceutical compositions disclosed herein can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Also disclosed are kits that comprise a composition comprising a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

Method of Screening

Also disclosed herein are methods of identifying a putative anti-cancer compound comprising contacting an cell expressing MC1R with a target compound and determining whether the compound binds the MC1R, wherein a compound that binds the MC1R is identified as a putative anti-cancer compound.

EXAMPLES

The following examples are set forth below to illustrate the methods and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Example 1

The $^{225}$Ac version of the ligand was synthesized with high radiochemical purity. More compounds can be synthesized as describe in FIG. 1, panel B. Similar methods are shown in FIGS. 11, 12, and 13.

Figure 2:
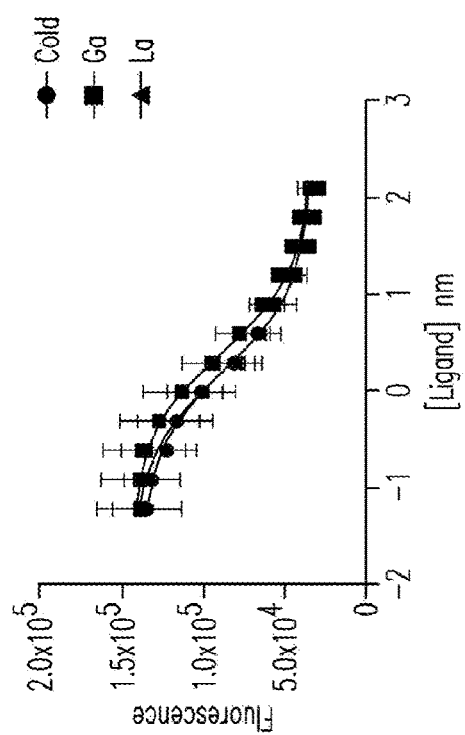
FIG. 2 is a graph from representative competitive binding assays of the $^{139}$La- and $^{69}$Ga-DOTA-MC1RL peptides. The binding affinities of unlabeled DOTA-MC1RL, $^{67/69}$Ga-DOTA-MC1RL and $^{139}$La-DOTA-MC1RL quantified as 0.24, 0.34 and 0.23 nM respectively.

High binding affinity of $^{139}$La-DOTA-MC1RL to MC1R (0.2 nM Ki) was observed. (FIG. 2). The radioactive conjugates are expected to have comparable affinities. A radiochemical yield greater than 95% and a radiochemical purity of 99.8% as determined by radio-TLC, radio-HPLC, and gamma-counter quantification (Table 1) was found.

TABLE 1

| Radiotracer | CPM | | Radiochemical Purity |
|---|---|---|---|
| | Origin | Front | |
| $^{225}$Ac(NO$_3$)$_3$ | 93.6 | 157816.5 | 100% (Front) |
| $^{225}$Ac-MC1RL-DOTA | 157920.3 | 307.2 | 99.8% (Origin) |

Figure 6A:
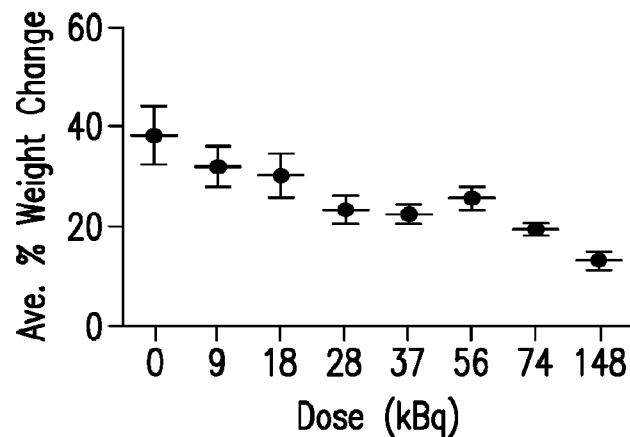
FIGS. 6A, 6B and 6C are graphs from a MTD study of $^{225}$Ac-DOTA-MC1RL radio-therapeutic agent.
Figure 6B:
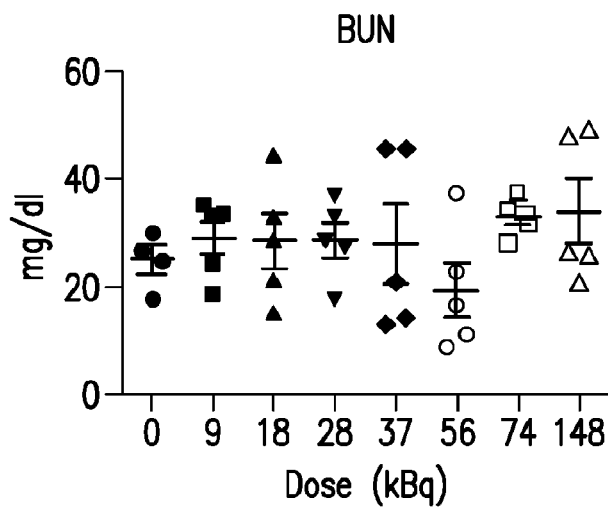
Figure 6C:
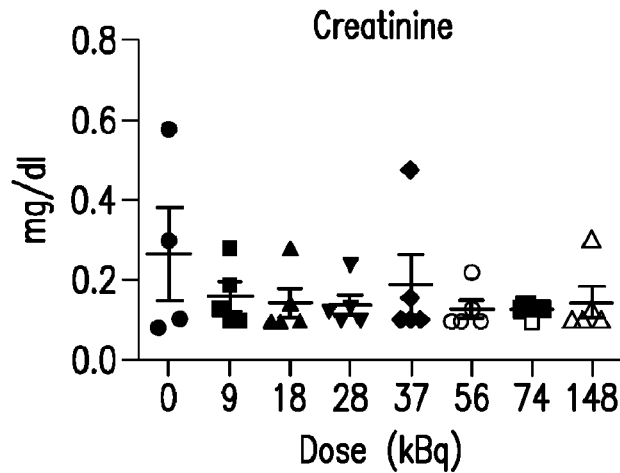

Moreover, $^{225}$Ac-DOTA-MC1RL showed excellent in vitro stability even after 10 days in human serum at 37° C. (Table 3). The MTD study showed no signs of altered behavior among the groups. All mice gained weight and appeared healthy but weight gain decreased with increased activity administered (FIG. 6A). Blood urea nitrogen (BUN) (FIG. 6B) and blood creatinine (FIG. 6C) levels, and pathology of a range of tissues including heart, lungs, brain, kidney and liver were all unremarkable. These results suggest that $^{225}$Ac-DOTA-MC1RL is tolerated extremely well.

Example 2

Figure 7:
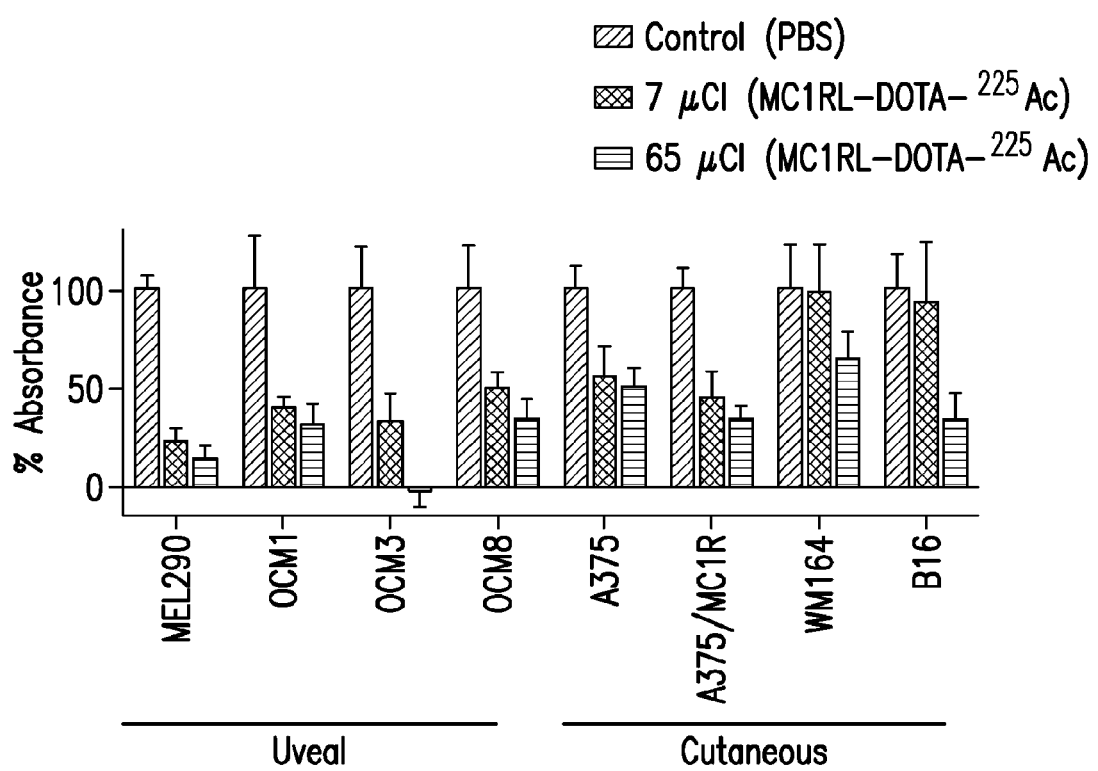
FIG. 7 is a graph from where MC1RL-DOTA-$^{225}$Ac and PBS (control) were added across a 96-well plate seeded with uveal and cutaneous cells with a range of MC1R expression values. After 5 min incubation with the agent the plates were washed 3 times and media added for 48 h incubation. After which the MTT assay was performed.
Figure 8:
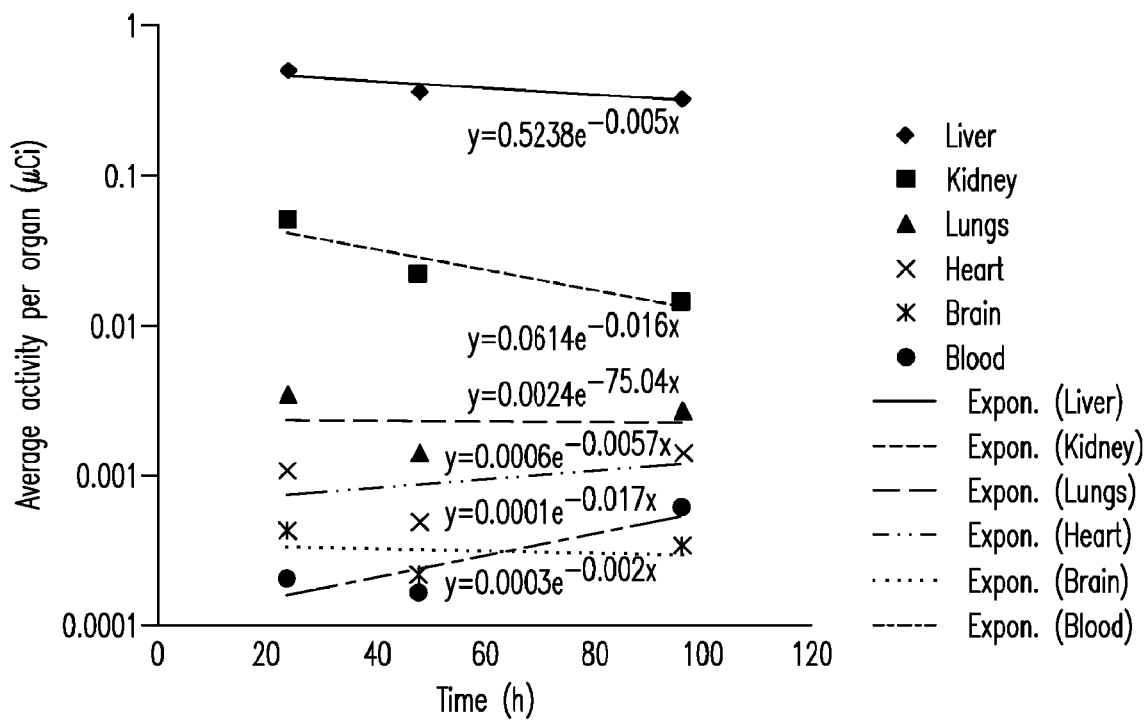
FIG. 8 is a graph of exponential line fits of BD data and estimated dose and clearance kinetics parameters in non-tumor bearing BALB/c mice. Mice were administered 2.3 to 3.1 µCi of MC1RL-DOTA-$^{225}$Ac. Groups of 6 animals were euthanized and organs harvested, weighed, gamma counted and gamma spectra generated for BD and dosimetry information at 24, 48 and 96 h.
Figure 9:
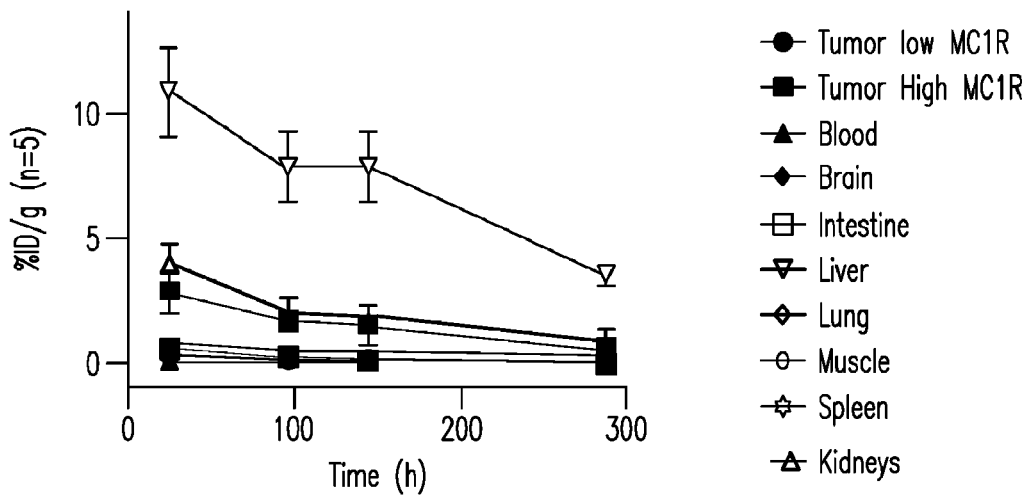
FIG. 9 is a graph from a BD study in tumor-bearing SCID mice. The mice were injected with A375/MC1R (75,000 MC1R on the surface) cells in the right flank and parental A375 cells (400 MC1R on the surface) in the left flank. Mice were administered 2 to 3.7 µCi of MC1RL-DOTA-$^{225}$Ac. Groups of 5 animals were euthanized and organs harvested, weighed, gamma counted and gamma spectra generated for BD and dosimetry information at: 24, 96, 144 and 288 h following administration of activity.

MC1RL-DOTA-$^{225}$Ac and PBS (control) were added across a 96-well plate seeded with uveal and cutaneous cells with a range of MC1R expression values. After 5 min incubation with the agent the plates were washed 3 times and media added for 48 h incubation at 37° C. After which the MTT assay was performed (FIG. 7).

Example 3

For PK and BD, non-tumor bearing BALB/c mice (n=5/group) were intravenously (i.v.) administered 2.3 to 3.1 µCi of $^{225}$Ac-DOTA-MC1RL. Blood, tissues and organs were collected over a time-course of 0, 24, 48 and 96 h.

Example 4

Figure 3:
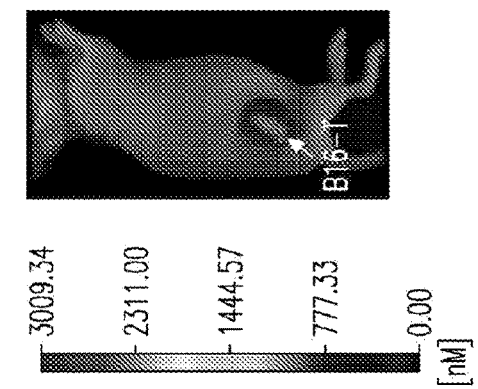
FIG. 3 contains data from in vivo targeting of a MC1R specific probe. Left mice: Representative images of normalized fluorescence intensity maps overlaid on mice bearing xenograft tumors. The control image (left mouse) shows lower fluorescence signal in the left flank tumor relative to the right flank tumor 4 h after intravenous injection of 3 nmol/kg of the MC1RL-800 probe. A blocking experiment (right mouse) was performed by coinjection of 0.25 µg unlabeled NDP-α-MSH and 3 nmol/kg of the MC1RL-800 probe. Inset on the far right graphs normalized fluorescence counts that significantly vary among low- and high-expressing tumors, and among tumors in control experiments compared to blocking experiments. Right mouse: Representative tomographic image of a mouse bearing a B16F10 xenograft tumor at 4 h after injection of 3 nmol/kg of the MC1RL-800 imaging probe using the FMT 2500 LX quantitative fluorescence tomography in vivo imaging system (PerkinElmer).
Figure 4:
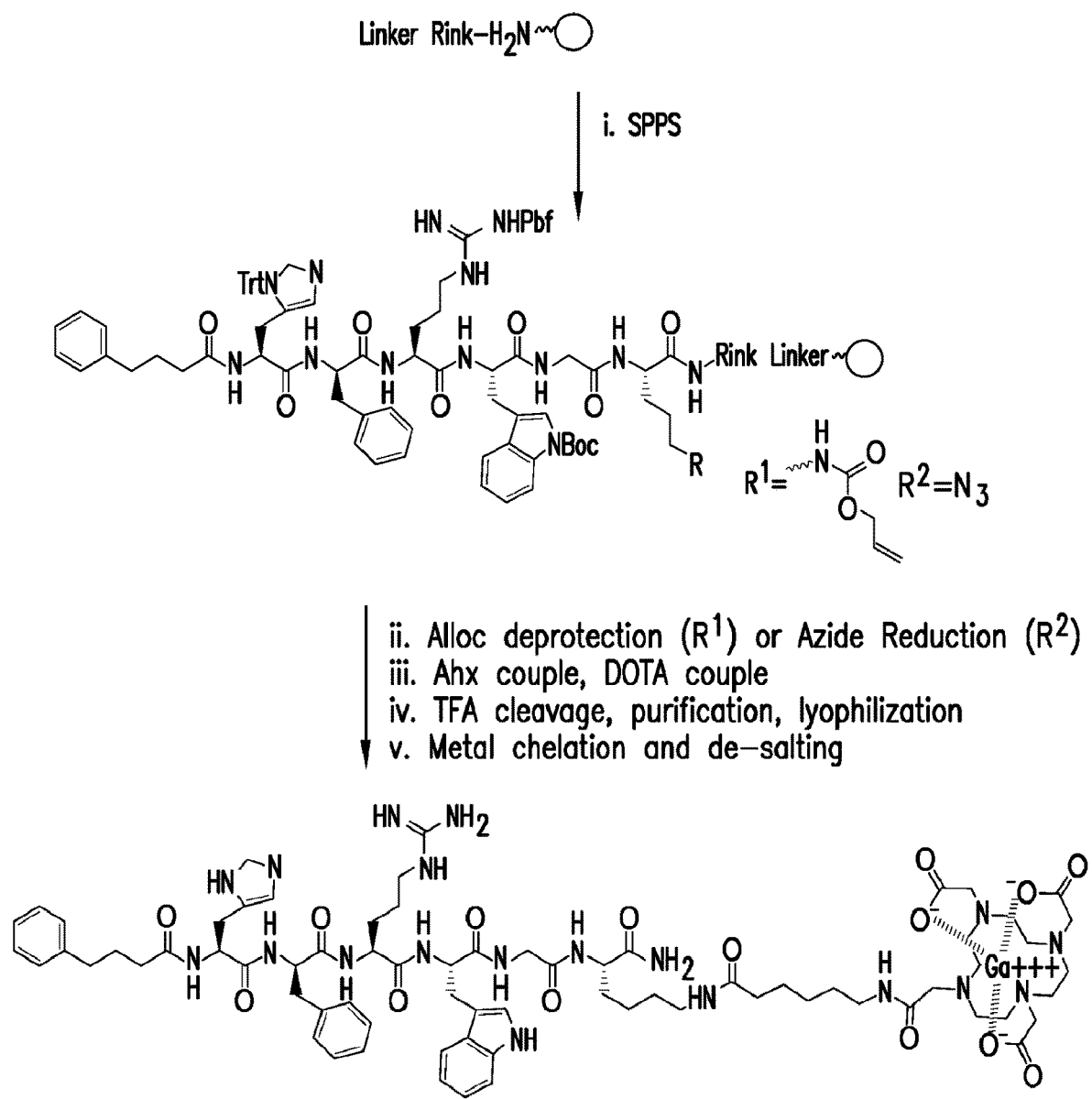
FIG. 4 is a schematic of the preparation of compounds as disclosed herein.

Previously, to investigate tumor targeting of the infrared conjugate of the ligand in vivo, bilateral subcutaneous xenograft tumors with A375/MC1R engineered cells in the right flank and A375 parental cells with relatively low MC1R expression in the left flank of nude mice and MC1RL-800 probe was injected intravenously and fluorescence accumulation was monitored over time. The A375 tumors with low MC1R expression had significantly lower normalized fluorescence signal compared to A375/MC1R tumors 4 h post-injection (P≤0.05, n=3). In vivo blocking studies were performed to determine that probe retention in the tumor was due to specific binding (FIG. 3, left mice). The accumulation of the probe in the mouse B16F10 tumor xenograft model with endogenous expression of MC1R is shown in FIG. 3, right mouse.

Example 5

1.9-3.3 µCi of MC1RL-DOTA-$^{225}$Ac, 1.8-2.7 µCi of scrambled peptide-DOTA-$^{225}$Ac, an excess of the cold agent (MC1RL-DOTA-$^{139}$La) and saline were injected to the SCID mice bearing A375/MC1R tumors injection (n=10 per group, volume of the tumors: 57-266 mm3). Mice were observed daily for health and twice per week weighed and tumor volumes measured by caliper. When the tumors reach 2000 mm$^3$ (experimental endpoint), animals were euthanized. Euthanizations prior to 2000 mm$^3$ were due to clinical endpoints, i.e. predominantly due to tumor ulceration.

Figure 10A:
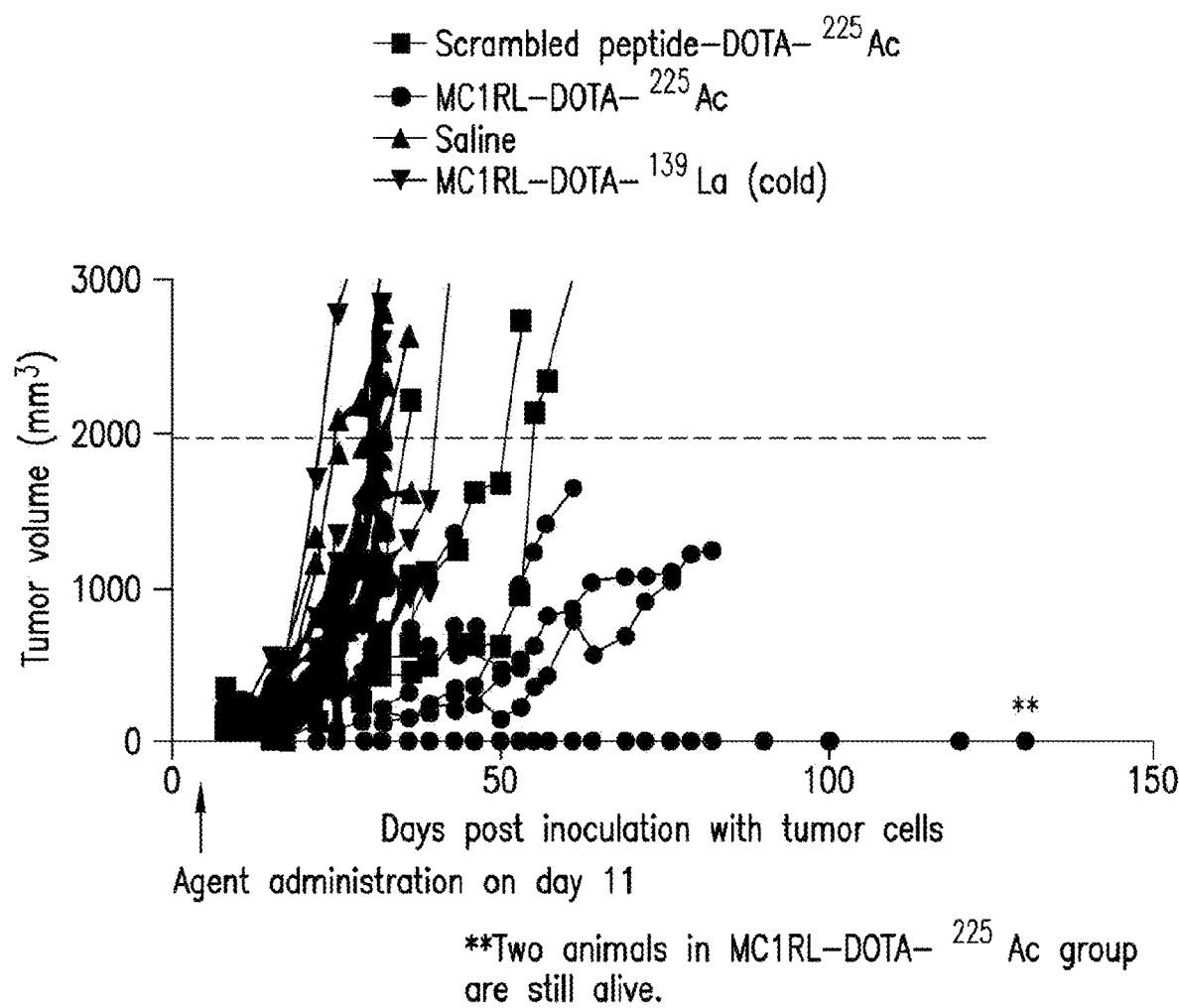
FIG. 10A, shows data from when 1.9-3.3 µCi of MC1RL-DOTA-$^{225}$Ac, 1.8-2.7 µCi of scrambled peptide-DOTA-$^{225}$Ac, an excess of the cold agent (MC1RL-DOTA-$^{139}$La) and saline were injected to the SCID mice bearing A375/MC1R tumors injection (n=10 per group, volume of the tumors: 57-266 mm$^3$). Mice were observed daily for health and twice per week weighed and tumor volumes measured by caliper. When the tumors reach 2000 mm$^3$ (experimental endpoint), animals were euthanized. Euthanizations prior to 2000 mm$^3$ were due to clinical endpoints, i.e. predominantly due to tumor ulceration.
Figure 10B:
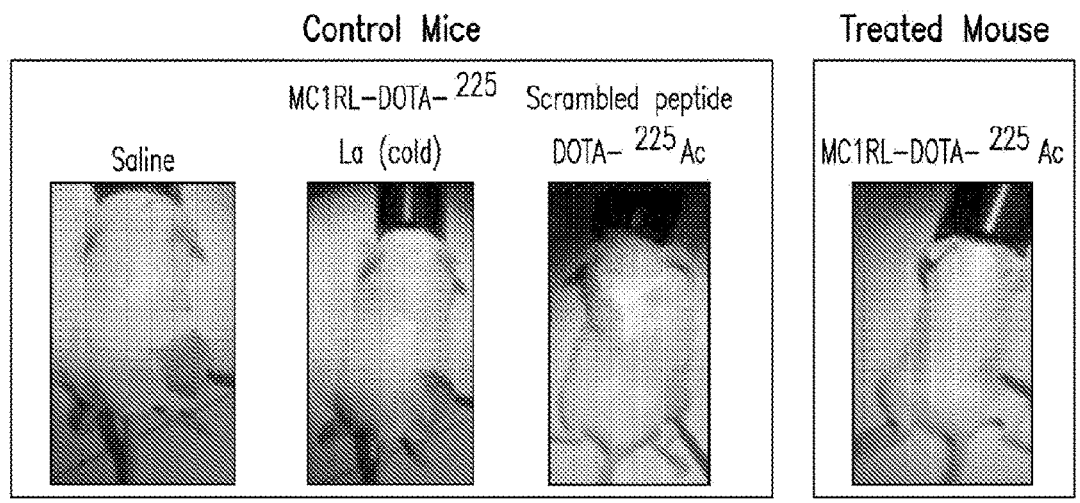
FIG. 10B is a representative images of control mice and a mouse treated with the agent at 22 days post-administration.
Figure 14:
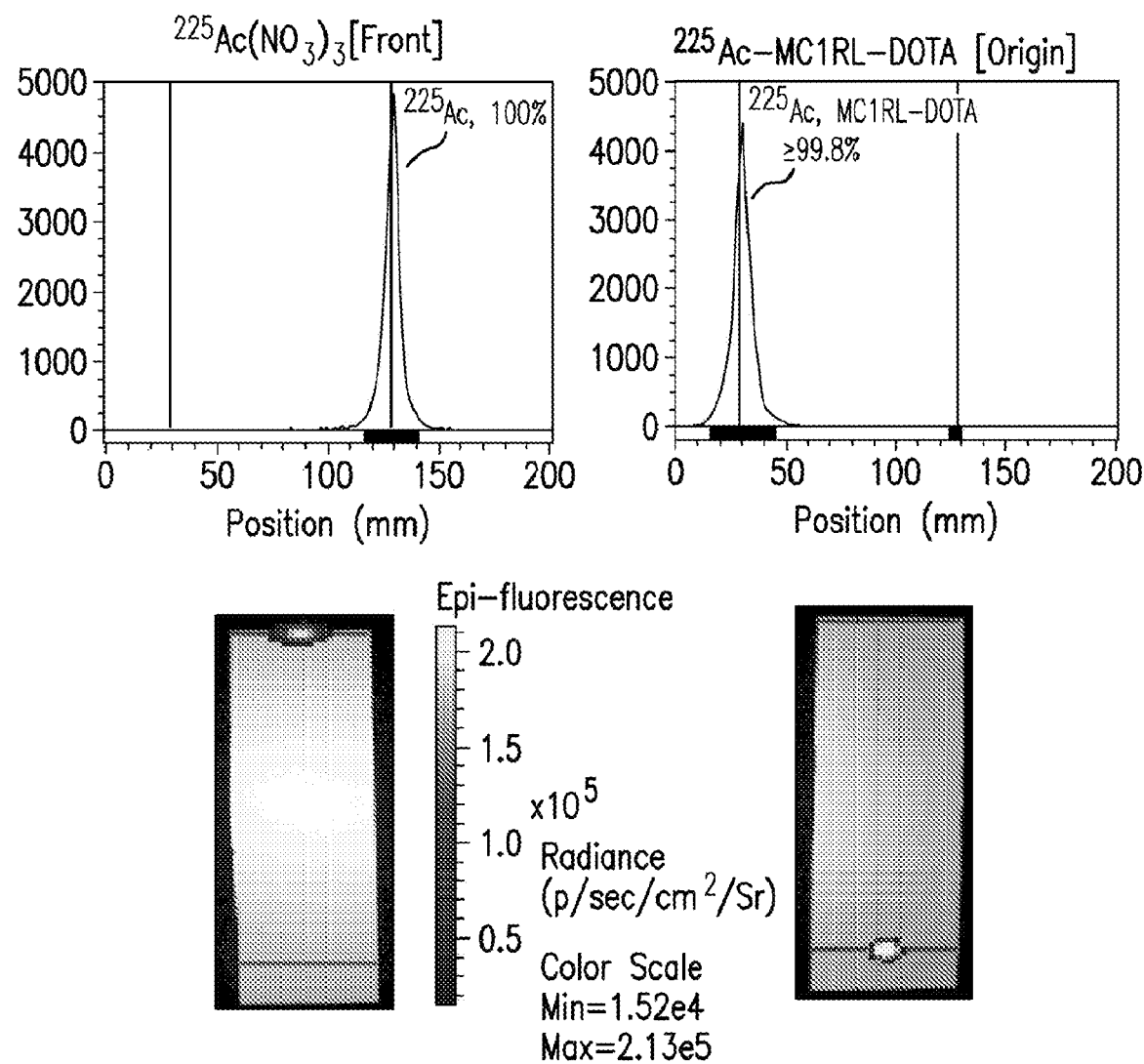
FIG. 14 shows the results from a radiochemical purity by radio-TLC and Cherenkov luminescence imaging (CLI) and Gamma-counter. Purity is greater than 99.8%.
Figure 15:
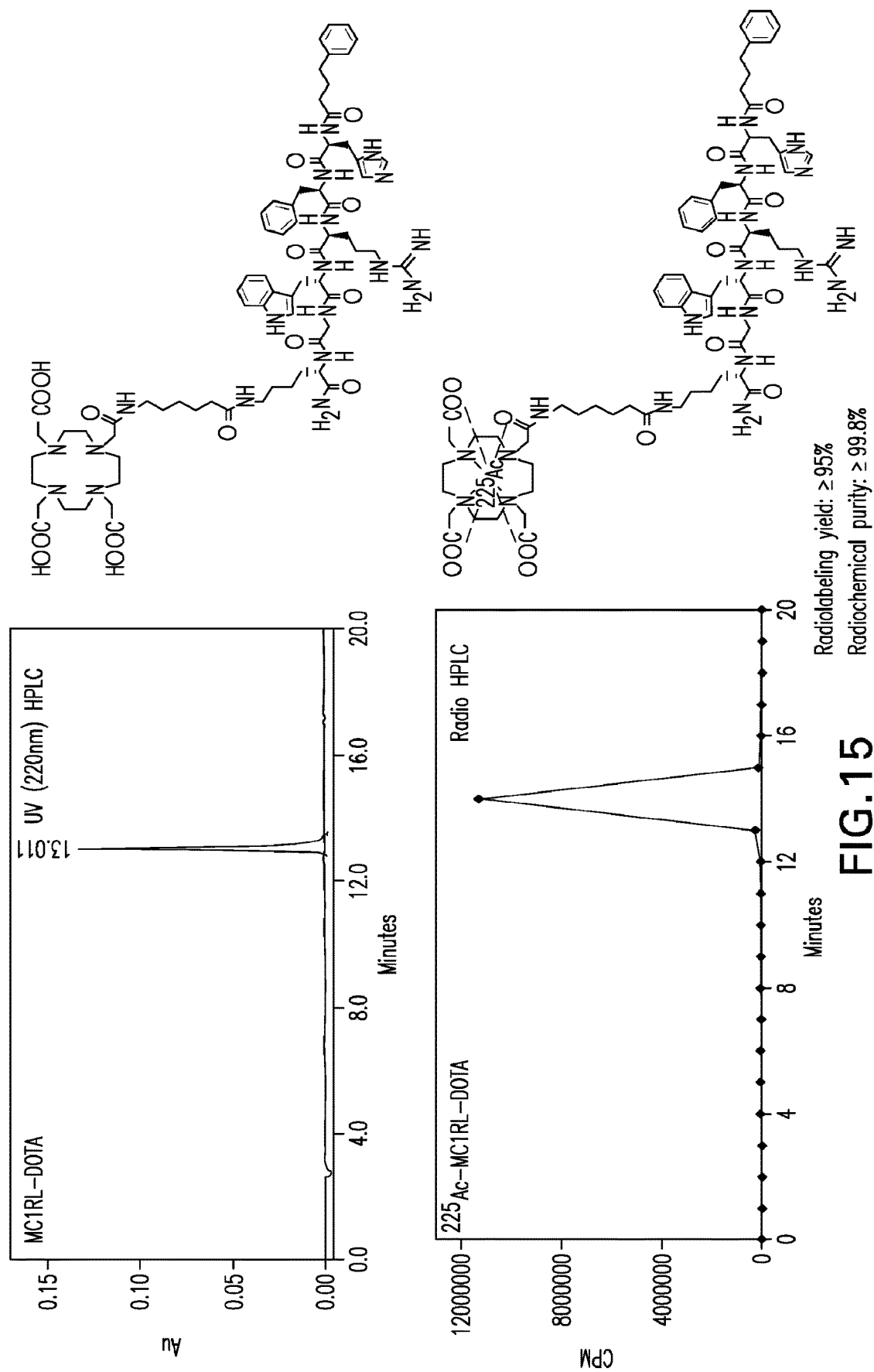
FIG. 15 is a pair of graphs showing the radiochemical yield and purity of compounds disclosed herein by Radio-HPLC.
Figure 20:
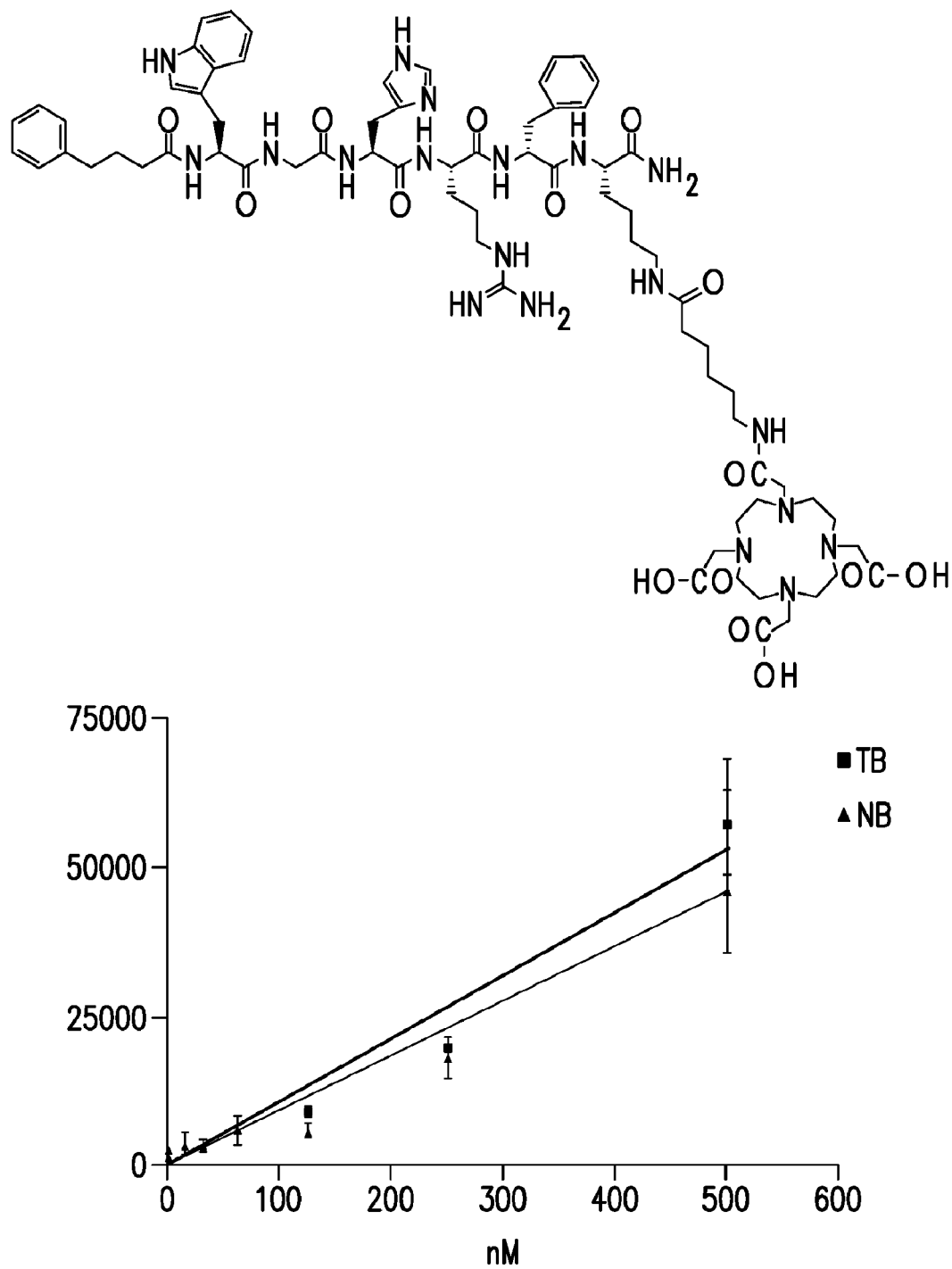
FIG. 20 top panel, shows scrambled MC1RL linked through Ahx to DOTA. The binding sequence is 1-Phenylbutyric acid-His(D)Phe-Arg-Trp-Gly-Lys(Ahx-DOTA)-

Representative images of control mice and a mouse treated with the agent at 22 days post-administration. Note that the three control mice have tumors that have progressed. The treated mouse no longer has a tumor in the shaved area of the flank. In each case, the red stick points to the shaved area on the flank (FIG. 10).

Discussion

Although RAF kinase inhibitors have substantial therapeutic effects in patients with BRAF-mutant melanoma, these agents are effective in a fraction of melanoma patients, only rarely do tumors regress completely, and the therapeutic effects are often temporary, due to the emergence of resistant populations. However, it was recently estimated in a computational study that combinations of targeted therapies could result in prolonged disease-free periods, or even be curative. Hence, novel targeted therapeutics are needed for treatment of metastatic melanoma. As an alternative to targeting agents against specific signal transduction pathways, tumor cells can be targeted by "smart bombs". Smart bombs act through the delivery of regionally toxic agents to a target that is over-expressed on the surface of the tumor cells, specifically killing both target expressing and adjacent non-expressing tumor and stroma. Such agents must have rapid clearance, and have high specificity for tumor retention, effectively increasing the therapeutic window and decreasing off-target toxicities. This is the promise of radioimmunotherapy, which has been particularly effective in blood cancers and are being increasingly developed for solid tumors. There is growing interest in the use of α-emitters, as compared with β-emitters, as they maximize damage at the target while reducing collateral damage and are less susceptible to radioresistance. Alpha particles travel along a very short path (on the order of a few cell diameters), and have a very high linear energy transfer, depositing large amounts of energy in the surroundings. Particularly for solid tumors, this leads to far more efficient cell killing (1-10 particle hits to kill a cell vs. thousands for beta). While many α-particle emitting radionuclides exist, few are used clinically because of incompatible half-lives, cost of production and limited availability. The most commonly used α-emitting radionuclides are $^{213}$Bi, $^{211}$At, $^{223}$Ra and $^{225}$Ac (11). $^{225}$Ac (t½= 10 d; Eαmax=6-8 MeV), which is commercially available from Oak Ridge National Laboratories, is well suited for targeted radiotherapy. Currently, targeted $^{225}$Ac therapy is being evaluated in numerous preclinical and clinical studies against a variety of malignancies with promising results. Phase II clinical results recently presented at the Congress of the European Cancer Organizations (ECCO) have shown that the targeted alpha emitter, Alpharadin, can increase survival and reduce pain associated with breast cancer bone metastases.

Patients with metastatic melanoma can be stratified with PET imaging using companion diagnostic agents prior to initiation of therapy. Therefore, patients who are more likely to respond positively to the corresponding targeted radiotherapies will be identified. The companion imaging agent will also allow physicians to non-invasively assess tumor response to therapy over time without subsequent biopsy.

It has been estimated that 80% of malignant melanomas express high levels of MC1R. The expression of MC1R through mRNA expression microarray and immunohistochemistry (IHC) analysis was previously investigated in melanoma patient samples and showed high expression of MC1R in melanoma patients. Further, MC1R has been reported as being expressed in 94% of uveal melanomas which is a subtype of melanoma that is lacking in effective treatments. MC1R is a member of a family of five G protein coupled melanocortin receptors (MC1R-MC5R), which bind melanocyte-stimulating hormone (MSH) and related ligands. Although, $^{212}$Pb/$^{212}$Bi coupled to alpha-MSH has been used to treat melanoma, α-MSH also targets MSH receptor family members that are expressed in a wide range of tissues and organs throughout the body, ranging from the kidneys and lungs (MC5R), adrenal glands (MC2R), and hypothalamus (MC3R/MC4R). Hence there is concern for normal tissue toxicity for this non-specific agent.

A high affinity (0.24 nM Ki) MC1R selective ligand was described with lower affinity for MC4R and MC5R, and modified this ligand with moieties to facilitate attachments. Near-infrared fluorescent (NIRF) dyes were also conjugated to this ligand and demonstrated high binding affinity (0.4±0.1 nM $K_i$) and in vivo specificity for tumors with endogenous levels of MC1R expression. In vivo fluorescence tomographic imaging and intravital confocal fluorescence microscopy were used to characterize the PK, BD and tumor cell uptake of these MC1R targeted NIRF conjugates. In addition, a compartmental mathematical model was developed to interpret the experimental data and to estimate the PK parameters for the whole animal.

Figure 1B:
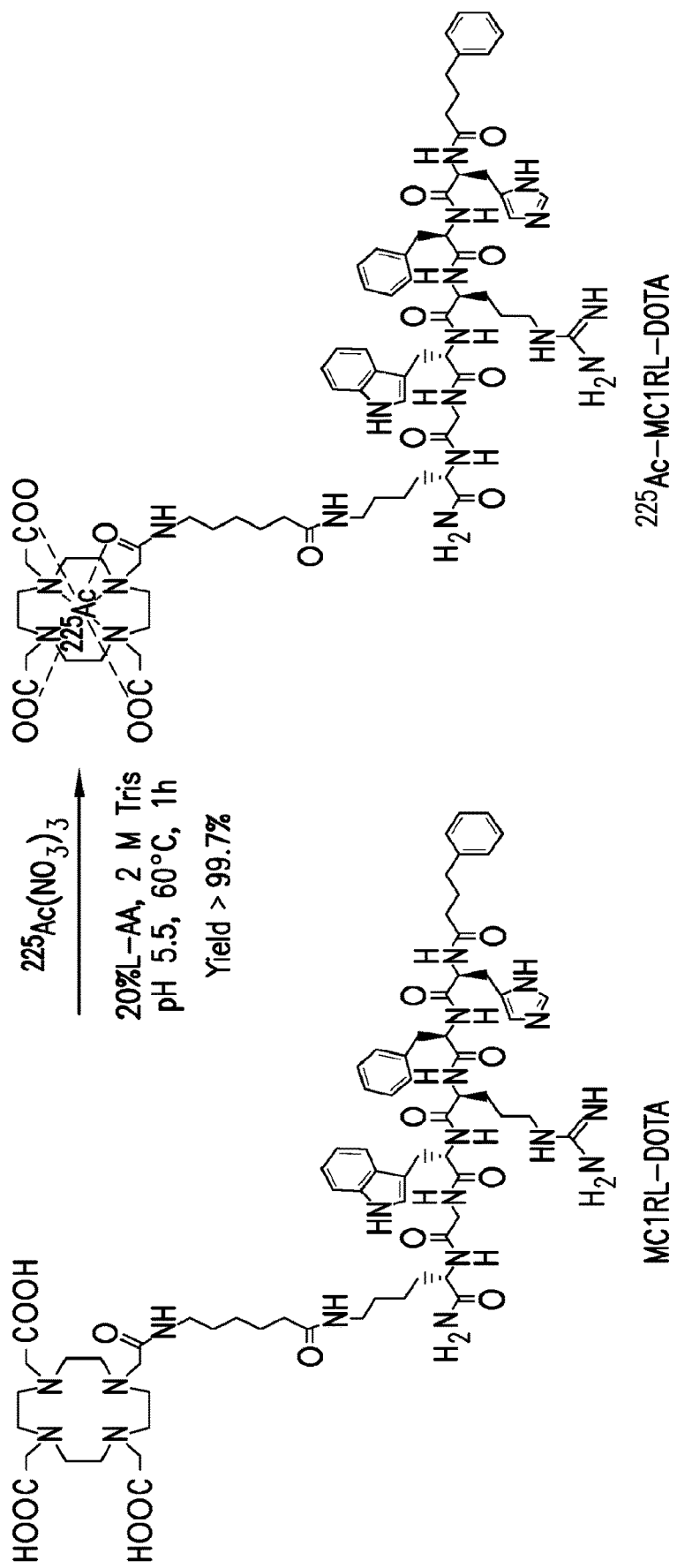
FIG. 1B shows the radiochemical synthesis scheme of $^{225}$Ac-DOTA-MC1RL.

These studies have demonstrated that the disclosed MC1R-specific targeting scaffold has excellent potential for development of a novel radiotherapeutic with a companion PET imaging agent for treatment of metastatic and uveal melanoma. A DOTA labeled conjugate of the MC1R specific ligand (DOTA-MC1RL) with $^{139}$La (as nonradioactive surrogate of the alpha particle emitting $^{225}$Ac) and $^{67/69}$Ga (as a nonradioactive surrogate of the PET radionuclide $^{68}$Ga) was synthesized as shown in FIG. 1, panel A. In this scheme, standard SPPS with alloc orthogonal protection: Steps 1-7, Fmoc deprotection: 20% Piperidine, 2% DBU in NMP; Fmoc-aa-OH (5 eq.), HCTU (5 eq.), NMM (15 eq.) in NMP for 1 h; Step 8, alloc deprotection: 5 mol % Pd(PPh$_3$)$_4$ in NMM, AcOH, CHCl$_3$ (1:2:37); Fmoc-Ahx-OH and DOTA coupled same above. Step 10a, Cleavage cocktail (2.5% H2O, 2.5% TIS, 95% TFA) treatment for 3 h, Step 10b 3× diethyl ether washes, lyophilization and RP-HPLC purification (0.1% TFA modifier). Step 11 Metal chelation (GaCl$_3$ or LaCl$_3$.7H$_2$O, 3 eq.) in 0.1M Ammonium Acetate, pH 8, incubated 2-4 h at room temperature. Chelation monitored by HPLC, MALDI-TOF, LC-QTOF; desalting by either RP-HPLC (0.1% TEA/AcOH, pH6) or C18 SPE cartridge. Since all four isotopes used are chemically similar, these four different chelates will have similar in vivo PK and BD profiles.

Time-resolved fluorescence (TRF) competition binding assays were performed to determine binding affinities of these DOTA conjugates (FIG. 2). The TRF method takes advantage of the long fluorescence lifetime of the lanthanide Europium and can detect less than one attomole in a multiwell plate sample. Hek293/MC1R cells (Hek293 cells engineered to over-express MC1R) were used for the binding assays. Saturation TRF binding assays were performed using versions of the compounds with chelated europium to determine specific and non-specific binding (FIG. 17-20).

DOTA-MC1RL was subsequently labeled with $^{225}$Ac ($^{225}$Ac-DOTA-MC1RL)(FIG. 1, panel B) and demonstrated high radiolabeling yield (≥95%), high purity (99.8%) as determined by CLI and radio-TLC and quantified by gamma-counter and radio-HPLC (Table 1).

In addition, high in vitro serum stability of the conjugate was observed (Table 2) by adding 50 μL of $^{225}$Ac-MC1RL-DOTA (56 μCi) to 1 mL of human serum. The solutions were incubated at 37° C. for 10 days and analyzed by TLC scanner (Bioscan) and quantified by gamma-counter.

TABLE 2

In vitro stability study. 225Ac-DOTA-MC1RL was incubated at 37° C. in human serum over a 10 day period of time.

| Day | % Intact | |
| --- | --- | --- |
| | TLC scanner | Gamma-counter |
| 0 | 100 | 100 |
| 2 | 97.3 ± 0.5 | 96.9 ± 0.4 |
| 4 | 95.6 ± 1.1 | 95.1 ± 0.8 |

SEQUENCE LISTING

```
<160> NUMBER OF SEQ ID NOS: 2

<210> SEQ ID NO 1
<211> LENGTH: 6
<212> TYPE: PRT
<213> ORGANISM: Artificial Sequence
<220> FEATURE:
<223> OTHER INFORMATION: Synthetic construct

<400> SEQUENCE: 1

His Phe Arg Trp Gly Lys
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic construct

<400> SEQUENCE: 2

Trp Gly His Arg Phe Lys
1               5
```

TABLE 2-continued

In vitro stability study. 225Ac-DOTA-MC1RL was incubated at 37° C. in human serum over a 10 day period of time.

| Day | % Intact | |
| --- | --- | --- |
| | TLC scanner | Gamma-counter |
| 6 | 93.5 ± 0.8 | 93.2 ± 1.3 |
| 8 | 91.4 ± 1.2 | 91.0 ± 0.9 |
| 10 | 90.2 ± 0.7 | 89.9 ± 1.3 |

The complete loss of tumor was observed in 22% of MC1RL-DOTA-$^{225}$Ac treated mice and these mice are still living (2 of 9 total) following a single intravenous administration (FIG. 10). These 2 mice are currently tumor free 150 days post injection. The other 7 treated mice were euthanized at an average of 86 days due to tumor ulceration without progression. While the median time-to-endpoint (tumor >2000 mm$^3$) of control mice treated with saline, MC1RL-DOTA-$^{139}$La (cold surrogate) and scrambled peptide-DOTA-$^{225}$Ac were 22, 24 and 32 days respectively after injection.

The methods and compositions of the appended claims are not limited in scope by the specific methods and compositions described herein, which are intended as illustrations of a few aspects of the claims and any methods and compositions that are functionally equivalent are within the scope of this disclosure. Various modifications of the methods and compositions in addition to those shown and described herein are intended to fall within the scope of the appended claims. Further, while only certain representative methods, compositions, and aspects of these methods and compositions are specifically described, other methods and compositions and combinations of various features of the methods and compositions are intended to fall within the scope of the appended claims, even if not specifically recited. Thus a combination of steps, elements, components, or constituents can be explicitly mentioned herein; however, all other combinations of steps, elements, components, and constituents are included, even though not explicitly stated.

What is claimed is:

1. A compound having the following structure:

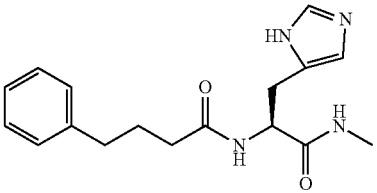

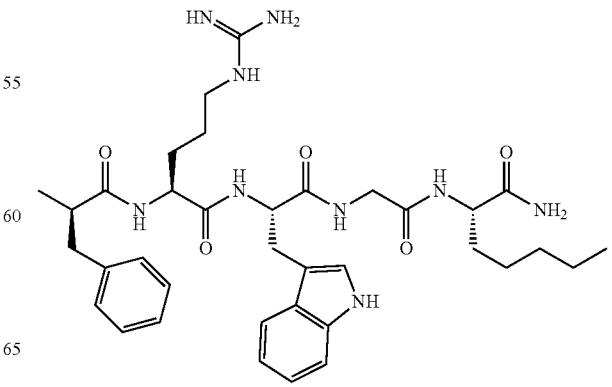

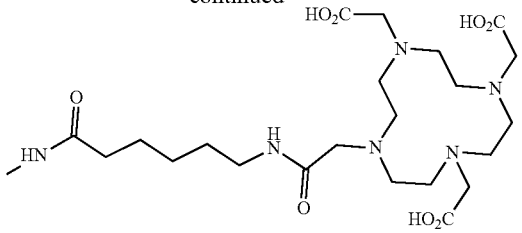

or a pharmaceutically acceptable salt thereof.

2. The compound of claim 1, further comprising a radionuclide.

3. The compound of claim 2, wherein the radionuclide is an alpha-particle or beta-particle emitter.

4. The compound of claim 2, wherein the radionuclide is selected from the group consisting of $^{90}$Y, $^{177}$Lu, $^{18}$F, $^{64}$Cu, $^{67}$Cu, $^{89}$Zr, $^{124}$I, $^{123}$I, $^{152}$Eu, $^{212}$Pb, and $^{99m}$Tc.

5. The compound of claim 2, wherein the radionuclide is selected from the group consisting of $^{225}$Ac, $^{68}$Ga, and $^{111}$In.

6. The compound of claim 2, wherein the radionuclide is $^{225}$Ac.

7. A composition comprising the compound of claim 1 and a pharmaceutically acceptable carrier.

8. A composition comprising the compound of claim 6 and a pharmaceutically acceptable carrier.

9. A method of treating a cancer in a subject, comprising administering to the subject an effective amount of the compound of claim 2.

10. The method of claim 9, wherein the cancer is metastatic melanoma.

11. The method of claim 9, wherein the cancer is uveal melanoma.

12. The method of claim 9, wherein the cancer is cutaneous melanoma.

* * * * *